(12) United States Patent
Murata et al.

(10) Patent No.: US 8,148,045 B2
(45) Date of Patent: Apr. 3, 2012

(54) OXIME ESTER COMPOUND AND PHOTOPOLYMERIZATION INITIATOR CONTAINING THE SAME

(75) Inventors: Kiyoshi Murata, Tokyo (JP); Takeo Oishi, Tokyo (JP); Koichi Kimijima, Tokyo (JP)

(73) Assignee: Adeka Corporation, Tokyo (JP)

( * ) Notice: Subject to any disclaimer, the term of this patent is extended or adjusted under 35 U.S.C. 154(b) by 13 days.

(21) Appl. No.: 12/950,275

(22) Filed: Nov. 19, 2010

(65) Prior Publication Data

US 2011/0129778 A1 Jun. 2, 2011

(30) Foreign Application Priority Data

Nov. 27, 2009 (JP) ................................. 2009-269801
Oct. 4, 2010 (JP) ................................. 2010-225063

(51) Int. Cl.
*G03F 7/00* (2006.01)
*G03F 7/004* (2006.01)
*G03F 7/028* (2006.01)
*C07C 69/16* (2006.01)
*C07C 321/30* (2006.01)

(52) U.S. Cl. .................. 430/270.1; 430/913; 430/281.1; 560/252; 560/18

(58) Field of Classification Search ............... 430/270.1, 430/281.1, 913; 560/18, 252
See application file for complete search history.

(56) References Cited

U.S. PATENT DOCUMENTS

| | | | |
|---|---|---|---|
| 6,596,445 B1 | 7/2003 | Matsumoto et al. | |
| 6,949,678 B2 | 9/2005 | Kunimoto et al. | |
| 7,189,489 B2 * | 3/2007 | Kunimoto et al. | 430/270.1 |
| 7,674,503 B2 * | 3/2010 | Sasaki | 427/510 |

FOREIGN PATENT DOCUMENTS

| | | | |
|---|---|---|---|
| EP | 2128132 A1 * | 12/2009 | |
| JP | 2000-80068 | 3/2000 | |
| JP | 2001-233842 | 8/2001 | |
| JP | 2001-302871 | 10/2001 | |
| JP | 2004-534797 | 11/2004 | |
| JP | 2005-25169 | 1/2005 | |
| JP | 2005-128483 | 5/2005 | |
| JP | 2005-242279 | 9/2005 | |
| JP | 2005-242280 | 9/2005 | |
| JP | 2006-16545 | 1/2006 | |
| JP | 2006-53569 | 2/2006 | |
| JP | 2008-003164 | 1/2008 | |
| JP | 2008-292903 | 12/2008 | |
| JP | 2009-251392 | 10/2009 | |
| WO | 2008-078686 | 7/2008 | |
| WO | 2009-131189 | 10/2009 | |

OTHER PUBLICATIONS

JP Notice of Rejection dated May 17, 2011.
European Search Report dated Mar. 23, 2011 in corresponding European Application No. 10015054.9.
Tarutani, Shinji et al., "Negative-working resists containing radiation-sensitive crosslinking accelerators and their patterning", XP002628097, retrieved from STN, Database accession No. 2009:1330295, Database Caplus (online), Chemical Abstracts Service, Columbus, OH, 2009.
XP002628098, Database accession No. 1239647-75-6, Database Registry (online), Chemical Abstracts Service, Columbus, OH, Sep. 1, 2010.

* cited by examiner

*Primary Examiner* — Amanda C. Walke
(74) *Attorney, Agent, or Firm* — Young & Thompson

(57) ABSTRACT

A novel compound is a highly-sensitive photopolymerization initiator with excellent stability, low sublimability, excellent developability, and high transmittance in the visible region. It efficiently absorbs, and is activated by, near-ultraviolet rays such as at 365 nm. Also provided are a photopolymerization initiator and a photosensitive composition using such compound. An oxime ester compound is represented by the following general formula (I), a photopolymerization initiator containing the same, and a photosensitive composition containing the photopolymerization initiator and a polymerizable compound having an ethylenically unsaturated bond:

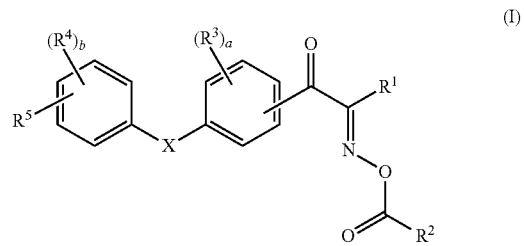

(I)

$R^1$ and $R^2$ each represent $R^{11}$, $COR^{11}$, $CONR^{12}R^{13}$, CN, etc.; $R^{11}$, $R^{12}$, and $R^{13}$ each represent a $C_{1-20}$ alkyl group, etc.; $R^3$ and $R^4$ each represent $R^{11}$, $OR^{11}$, $COR^{11}$, $CONR^{12}R^{13}$, $OCOR^{11}$, CN, a halogen atom, etc.; a and b each represent an integer 0-4; X represents an oxygen atom, a sulfur atom, etc.; and $R^5$ represents OH, COOH, or a group represented by general formula (II).

19 Claims, No Drawings

OXIME ESTER COMPOUND AND PHOTOPOLYMERIZATION INITIATOR CONTAINING THE SAME

TECHNICAL FIELD

The present invention relates to a novel oxime ester compound useful as a photopolymerization initiator used in a photosensitive composition, a photopolymerization initiator containing the oxime ester compound, and a photosensitive composition made by adding a polymerizable compound having an ethylenically unsaturated bond to the photopolymerization initiator.

BACKGROUND ART

Photosensitive compositions are prepared by adding a photopolymerization initiator to a polymerizable compound having at least one ethylenically unsaturated bond. Because such photosensitive compositions can be cured through polymerization through irradiation with energy rays (light), they are used, for example, in photocurable inks, photosensitive printing plates, and various types of photoresists.

The following Patent Documents 1 to 11 propose the use of oxime ester compounds as photopolymerization initiators used for photosensitive compositions.

While some of the oxime ester compounds disclosed in those Patent Documents have satisfactory sensitivity, such oxime ester compounds unfortunately have poor transmittance in the visible region and thus cannot provide the desired colors when used in color filters. (Particularly in transparent photosensitive compositions, such as protection films, and in color-filter resists containing blue pigments or colorants, the brightness and color purity deteriorate in cases where compounds having absorption in the range of 380 to 450 nm are mixed.) On the other hand, oxime ester compounds having high transmittance in the visible region are, in turn, unsatisfactory in terms of sensitivity. Thus, there has been a demand for a photopolymerization initiator having both satisfactory sensitivity and high transmittance in the visible region.

Meanwhile, high sensitivity is demanded of alkali-developable, colored photosensitive resin compositions containing colorants, such as color filers, which thus calls for high photopolymerization-initiator concentrations in resists.

High concentrations of photopolymerization initiators, however, give rise to residues due to deterioration in developability and cause contamination of photomasks and heating furnaces due to sublimed products.

Citation List
Patent Document

Patent Document 1: JP-A-2000-80068 (U.S. Pat. No. 6,596,445)

Patent Document 2: JP-A-2001-233842 (U.S. Pat. No. 6,949,678)

Patent Document 3: JP-A-2001-302871

Patent Document 4: JP-T-2004-534797 (U.S. Pat. No. 7,189,489)

Patent Document 5: JP-A-2005-25169

Patent Document 6: JP-A-2005-128483

Patent Document 7: JP-A-2005-242279

Patent Document 8: JP-A-2005-242280

Patent Document 9: JP-A-2006-16545

Patent Document 10: JP-A-2008-3164

Patent Document 11: Japanese Patent No. 3,754,065

SUMMARY OF THE INVENTION

Problem to be Solved by the Invention

Thus, there still has been no photopolymerization initiator having satisfactory sensitivity and also high transmittance in the visible region.

Accordingly, the present invention aims at providing a novel compound useful as a highly-sensitive photopolymerization initiator that has excellent stability, low sublimability, excellent developability, and high transmittance in the visible region and that efficiently absorbs, and is activated by, near-ultraviolet rays such as at 365 nm, and also aims at providing a photopolymerization initiator and a photosensitive composition using such a compound.

Means for Solving the Problem

The present invention achieves the above object by providing a novel oxime ester compound represented by the following general formula (I) and a photopolymerization initiator containing the same:

[Chem. 1]

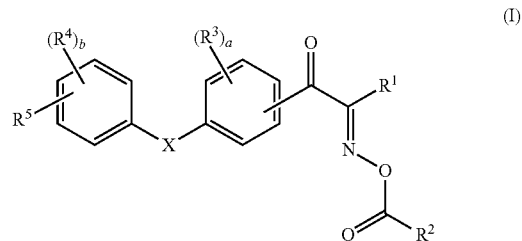

(I)

wherein, $R^1$ and $R^2$ each independently represent $R^{11}$, $OR^{11}$, $COR^{11}$, $SR^{11}$, $CONR^{12}R^{13}$, or CN;

$R^{11}$, $R^{12}$, and $R^{13}$ each independently represent a hydrogen atom, a $C_{1-20}$ alkyl group, a $C_{6-30}$ aryl group, a $C_{7-30}$ arylalkyl group, or a $C_{2-20}$ heterocyclic group;

a hydrogen atom in the substituents represented by $R^{11}$, $R^{12}$, and $R^{13}$ may optionally be substituted by $OR^{21}$, $COR^{21}$, $SR^{21}$, $NR^{22}R^{23}$, $CONR^{22}R^{23}$, $-NR^{22}-OR^{23}$, $-NCOR^{22}-OCOR^{23}$, $-C(=N-OR^{21})-R^{22}$, $-C(=N-OCOR^{21})-R^{22}$, CN, a halogen atom, or $COOR^{21}$;

$R^{21}$, $R^{22}$, and $R^{23}$ each independently represent a hydrogen atom, a $C_{1-20}$ alkyl group, a $C_{6-30}$ aryl group, a $C_{7-30}$ arylalkyl group, or a $C_{2-20}$ heterocyclic group;

a hydrogen atom in the substituents represented by $R^{21}$, $R^{22}$, and $R^{23}$ may optionally be substituted by CN, a halogen atom, a hydroxyl group, or a carboxyl group;

an alkylene portion in the substituents represented by $R^{11}$, $R^{12}$, $R^{13}$, $R^{21}$, $R^{22}$, and $R^{23}$ may be interrupted 1 to 5 times by —O—, —S—, —COO—, —OCO—, —NR$^{24}$—, —NR$^{24}$COO—, —OCONR$^{24}$—, —SCO—, —COS—, —OCS—, or —CSO—;

$R^{24}$ represents a hydrogen atom, a $C_{1-20}$ alkyl group, a $C_{6-30}$ aryl group, a $C_{7-30}$ arylalkyl group, or a $C_{2-20}$ heterocyclic group;

an alkyl portion in the substituents represented by $R^{11}$, $R^{12}$, $R^{13}$, $R^{21}$, $R^{22}$, and $R^{23}$ may have a branched side chain or may be a cyclic alkyl; $R^{12}$ and $R^{13}$, as well as $R^{22}$ and $R^{23}$, may together form a ring;

$R^3$ and $R^4$ each independently represent $R^{11}$, $OR^{11}$, $SR^{11}$, $COR^{11}$, $CONR^{12}R^{13}$, $NR^{12}COR^{11}$, $OCOR^{11}$, $COOR^{11}$, $SCOR^{11}$, $OCSR^{11}$, $COSR^{11}$, $CSOR^{11}$, CN, or a halogen atom;

a and b each independently represent an integer of 0 to 4;

X represents an oxygen atom, a sulfur atom, a selenium atom, $CR^{31}R^{32}$, CO, $NR^{33}$, or $PR^{34}$;

$R^{31}$, $R^{32}$, $R^{33}$, and $R^{34}$ each independently represent a hydrogen atom, a $C_{1-20}$ alkyl group, a $C_{6-30}$ aryl group, or a $C_{7-30}$ arylalkyl group;

an alkyl portion in the substituents represented by $R^{31}$, $R^{32}$, $R^{33}$, and $R^{34}$ may have a branched side chain or may be a cyclic alkyl; $R^{31}$, $R^{32}$, $R^{33}$, and $R^{34}$ may each independently form a ring together with one of the adjacent benzene rings; and $R^5$ represents OH, COOH, or a group represented by the following general formula (II);

[Chem .2]

(II)

wherein, $Z^1$ is a bonding hand and represents —O—, —S—, —$NR^{22}$—, —$NR^{22}$CO—, —$SO_2$—, —CS—, —OCO—, or —COO—;

$Z^2$ is a bonding hand and represents a $C_{1-20}$ alkyl group, a $C_{6-30}$ aryl group, a $C_{7-30}$ arylalkyl group, or a $C_{2-20}$ heterocyclic group, each of which being substituted by one to three of $R^6$;

an alkylene portion in the bonding hand represented by $Z^2$ may be interrupted 1 to 5 times by —O—, —S—, —COO—, —OCO—, —$NR^{22}$—, —$NR^{22}$COO—, —$OCONR^{22}$—, —SCO—, —COS—, —OCS—, or —CSO—; an alkylene portion in the bonding hand represented by $Z^2$ may have a branched side chain or may be a cyclic alkylene;

$R^6$ represents $OR^{41}$, $SR^{41}$, $CONR^{42}R^{43}$, $NR^{42}COR^{43}$, $OCOR^{41}$, $COOR^{41}$, $SCOR^{41}$, $OCSR^{41}$, $COSR^{41}$, $CSOR^{41}$, CN, or a halogen atom;

$R^{41}$, $R^{42}$, and $R^{43}$ each independently represent a hydrogen atom, a $C_{1-20}$ alkyl group, a $C_{6-30}$ aryl group, or a $C_{7-30}$ arylalkyl group; an alkyl portion in the substituents represented by $R^{41}$, $R^{42}$, and $R^{43}$ may have a branched side chain or may be a cyclic alkyl; $R^{42}$ and $R^{43}$ may together form a ring; and c represents an integer of 1 to 3.

The invention also provides a photosensitive composition, containing the above-described photopolymerization initiator and a polymerizable compound having an ethylenically unsaturated bond.

The invention further provides an alkali-developable photosensitive resin composition, containing the above-described photosensitive composition and an alkali-developable compound that may optionally have an ethylenically unsaturated group.

The invention also provides an alkali-developable, colored photosensitive resin composition, containing the above-described alkali-developable photosensitive resin composition and a colorant.

The present invention also provides a cured product produced by irradiating the above-described photosensitive composition, the above-described alkali-developable photosensitive resin composition, or the above-described alkali-developable, colored photosensitive resin composition, with energy rays.

Effects of the Invention

The oxime ester compound of the present invention has high transmittance in the visible region, low sublimability, and excellent developability, efficiently produces radicals on irradiation with emission lines such as at 365 nm ("i-lines"), and is useful as a photopolymerization initiator for photosensitive compositions.

BEST MODE FOR CARRYING OUT THE INVENTION

Preferred embodiments of oxime ester compounds according to the present invention and photopolymerization initiators containing the same will be described in detail below.

The oxime ester compound of the present invention is a novel compound represented by general formula (I) shown above. Note that geometrical isomers of the oxime ester compounds owing to the presence of the double bond in the oxime are not particularly distinguished.

In other words, the compound represented by general formula (I), the compound represented by general formula (III) described further below as a preferred embodiment of the present compound, and exemplary compounds thereof may represent either one of the geometrical isomers or mixtures of the isomers, and are thus not to be limited to the structures illustrating one of the isomers.

Examples of the $C_{1-20}$ alkyl group represented by $R^{11}$, $R^{12}$, $R^{13}$, $R^{21}$, $R^{22}$, $R^{23}$, $R^{24}$, $R^{31}$, $R^{32}$, and $R^{34}$ in general formula (I) and $R^{22}$, $R^{41}$, $R^{42}$, and $R^{43}$ in general formula (II) include methyl, ethyl, propyl, isopropyl, butyl, isobutyl, s-butyl, t-butyl, amyl, isoamyl, t-amyl, hexyl, heptyl, octyl, isooctyl, 2-ethylhexyl, t-octyl, nonyl, isononyl, decyl, isodecyl, undecyl, dodecyl, tetradecyl, hexadecyl, octadecyl, eicosyl, cyclopentyl, cyclohexyl, and cyclohexylmethyl.

Examples of the $C_{6-30}$ aryl group represented by $R^{11}$, $R^{12}$, $R^{13}$, $R^{21}$, $R^{22}$, $R^{23}$, $R^{24}$, $R^{31}$, $R^{32}$, $R^{33}$, and $R^{34}$ in general formula (I) and $R^{22}$, $R^{41}$, $R^{42}$, and $R^{43}$ in general formula (II) include phenyl, tolyl, xylyl, ethylphenyl, naphthyl, anthryl, and phenanthrenyl, and also substituted phenyl, biphenylyl, naphthyl, anthryl, etc., substituted at one or more positions by the above-described alkyl group.

Examples of the $C_{7-30}$ arylalkyl group represented by $R^{11}$, $R^{12}$, $R^{13}$, $R^{21}$, $R^{22}$, $R^{23}$, $R^{24}$, $R^{31}$, $R^{32}$, $R^{33}$, and $R^{34}$ in general formula (I) and $R^{22}$, $R^{41}$, $R^{42}$, and $R^{43}$, in general formula (II) include benzyl, α-methylbenzyl, α,α-dimethylbenzyl, and phenylethyl.

Preferred examples of the $C_{2-20}$ heterocyclic group represented by $R^{11}$, $R^{12}$, $R^{13}$, $R^{21}$, $R^{22}$, $R^{23}$, and $R^{24}$ in general formula (I) include 5 to 7-membered heterocycles such as pyridyl, pyrimidyl, furyl, thienyl, tetrahydrofuryl, dioxolanyl, benzoxazol-2-yl, tetrahydropyranyl, pyrrolidyl, imidazolidyl, pyrazolidyl, thiazolidyl, isothiazolidyl, oxazolidyl, isooxazolidyl, piperidyl, piperazyl, and morpholinyl.

Preferred examples of the ring that may be formed by $R^{12}$ and $R^{13}$ or by $R^{22}$ and $R^{23}$ in general formula (I), the ring that may be formed by $R^{42}$ and $R^{43}$ in general formula (II), and the ring that may be formed by $R^{31}$, $R^{32}$, $R^{33}$, or $R^{34}$ bonding to one of the adjacent benzene rings, include 5 to 7-membered rings such as a cyclopentane ring, a cyclohexane ring, a cyclopentene ring, a benzene ring, a piperidine ring, a morpholine ring, a lactone ring, and a lactam ring.

$Z^2$ in general formula (II) represents a $C_{1-20}$ alkyl group, a $C_{6-30}$ aryl group, a $C_{7-30}$ arylalkyl group, or a $C_{2-20}$ heterocyclic group, each of which being substituted by one to three of $R^6$.

Examples of the $C_{1-20}$ alkyl group substituted by one to three of $R^6$ include, e.g. when c=1, alkylene groups such as methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, octylene, nonylene, decylene, dodecylene, tridecylene, tetradecylene, pentadecylene, ethane-1,1-diyl, and propane-2,2-diyl.

Examples of the $C_{6-30}$ aryl group substituted by one to three of $R^6$ include, e.g. when c=1, arylene groups such as 1,2-phenylene, 1,3-phenylene, 1,4-phenylene, 2,6-naphthylene, 1,4-naphthylene, 2,5-dimethyl-1,4-phenylene, diphenylmethane-4,4'-diyl, 2,2-diphenylpropane-4,4'-diyl, diphenyl sulfide-4,4'-diyl, and diphenylsulfone-4,4'-diyl.

Examples of the $C_{7-30}$ arylalkyl group substituted by one to three of $R^6$ include, e.g. when c=1, arylalkylene groups such as the linking group represented by Chem. 3 below.

[Chem. 3]

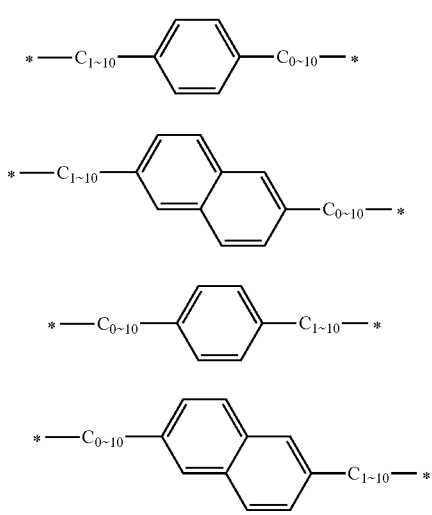

Examples of the $C_{2-20}$ heterocyclic group substituted by one to three of $R^6$ include, e.g. when c=1, divalent heterocyclic groups such as 2,5-pyridinediyl, 2,6-pyridinediyl, 2,5-pyrimidinediyl, 2,5-thiophendiyl, 3,4-tetrahydrofurandiyl, 2,5-tetrahydrofurandiyl, 2,5-furandiyl, 3,4-thiazolediyl, 2,5-benzofurandiyl, 2,5-benzothiophendiyl, N-methylindole-2, 5-diyl, 2,5-benzothiazolediyl, and 2,5-benzoxazolediyl.

The halogen atom represented by $R^3$ and $R^4$ in general formula (I) and by $R^6$ in general formula (II) and the halogen atom that may substitute $R^{11}$, $R^{12}$, $R^{13}$, $R^{21}$, $R^{22}$, and $R^{23}$ in general formula (I) include fluorine, chlorine, bromine, and iodine.

The alkylene portion in the substituents represented by $R^{11}$, $R^{12}$, $R^{13}$, $R^{21}$, $R^{22}$, and $R^{23}$ in general formula (I) and in the bonding hand represented by $Z^2$ in general formula (II) may be interrupted 1 to 5 times by —O—, —S—, —COO—, —OCO—, —NR$^{22}$—, —NR$^{22}$CO—, —NR$^{22}$COO— OCONR$^{22}$—, —SCO—, —COS—, —OCS—, or —CSO—, wherein the interrupting bonding group may include one or more types of groups, and, where possible, two or more bonding groups may continuously interrupt the above substituent/portion.

Further, the alkyl (alkylene) portion in the substituents represented by $R^{11}$, $R^{12}$, $R^{13}$, $R^{21}$, $R^{22}$, $R^{23}$, $R^{31}$, $R^{32}$, $R^{33}$, and $R^{34}$ in general formula (I), in the bonding hand represented by $Z^2$, and in the substituents represented by $R^{41}$, $R^{42}$, and $R^{43}$ in general formula (II) may have a branched side chain or may be a cyclic alkyl (alkylene).

Of the various oxime ester compounds according to the present invention, the following compounds have high sensitivity and are easy to produce, and are thus preferable:

a compound wherein X in general formula (I) is a sulfur atom or NR$^{33}$, R$^{33}$ in the same formula is a $C_{1-20}$ alkyl group that may have a branched side chain or that may be a cyclic alkyl;

a compound represented by the following general formula (III):

[Chem. 4]

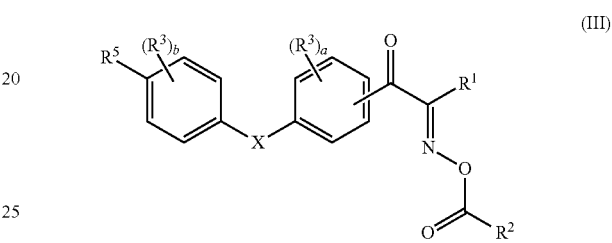

wherein, $R^1$, $R^2$, $R^3$, $R^4$, $R^5$, X, a, and b are the same as those in general formula (I); and a compound wherein $Z^1$ in general formula (II) is —O— or —OCO—.

Also, of the various oxime ester compounds according to the present invention, the following compounds have excellent developability, and are thus preferable:

a compound wherein $R^5$ in general formulas (I) and (III) is OH or COOH;

a compound wherein $R^6$ in general formula (II) is OH or COOH, and particularly a compound where c=1 in the same formula; and a compound wherein $Z^2$ in general formula (II) is a $C_{1-20}$ alkyl group substituted by one to three of $R^6$ and wherein the alkylene portion in the alkyl group may be interrupted 1 to 5 times by —O—, —OCO—, or —COO—, and particularly, a compound wherein $Z^2$ is a $C_{1-20}$ alkylene group and the methylene group in the alkylene group is interrupted 1 to 5 times by —O—.

Further, of the various oxime ester compounds according to the present invention, a compound wherein the hydrogen at the end of $Z^2$ has been substituted by $R^6$ in general formula (II) is easy to produce and is thus preferable. Note that a "hydrogen atom at the end" as used herein refers to the following: (1) in cases where the substituent is an alkyl group, a hydrogen atom of the methyl group at the end of the alkyl chain whose number of carbon atoms from the bonding point is the largest; (2) in cases where the substituent is a non-substituted ring structure, all the hydrogen atoms bonded to the ring; and (3) in cases where the substituent has a ring structure further substituted by an alkyl group, a hydrogen atom of the methyl group at the end of the alkyl chain further substituting the ring.

Accordingly, preferred concrete examples of the oxime ester compounds of the present invention represented by general formula (I) include the following compounds Nos. 1 to 108, although the present invention is not limited thereto:

[Chem. 5]
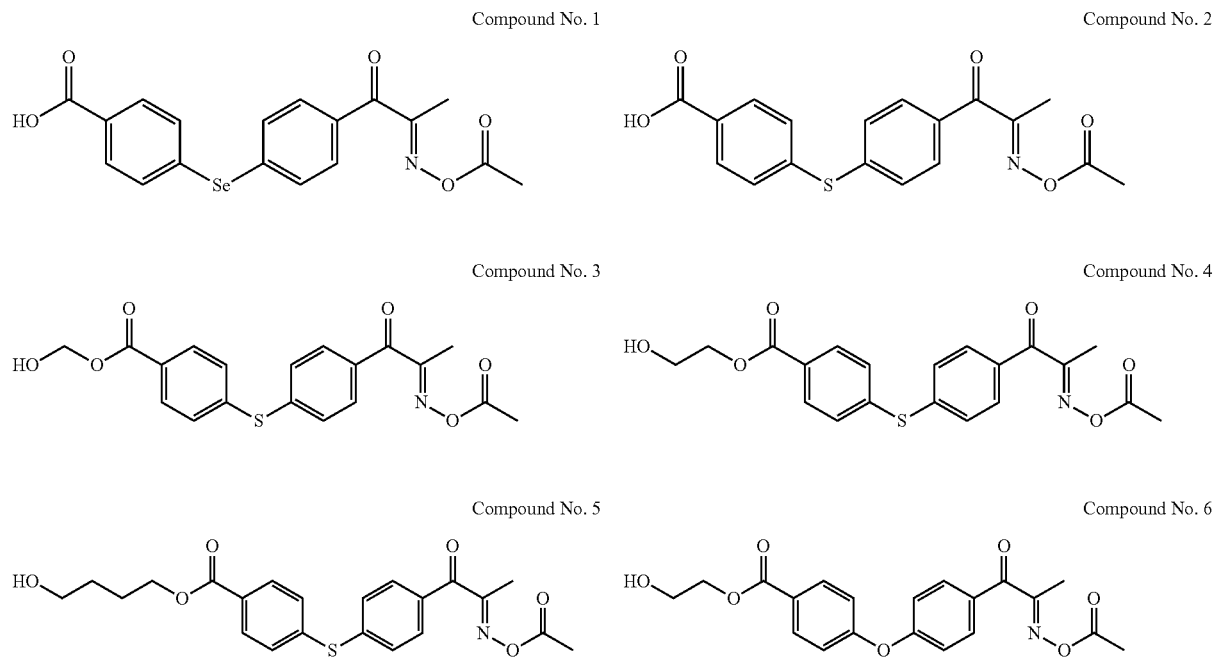
[Chem. 6]
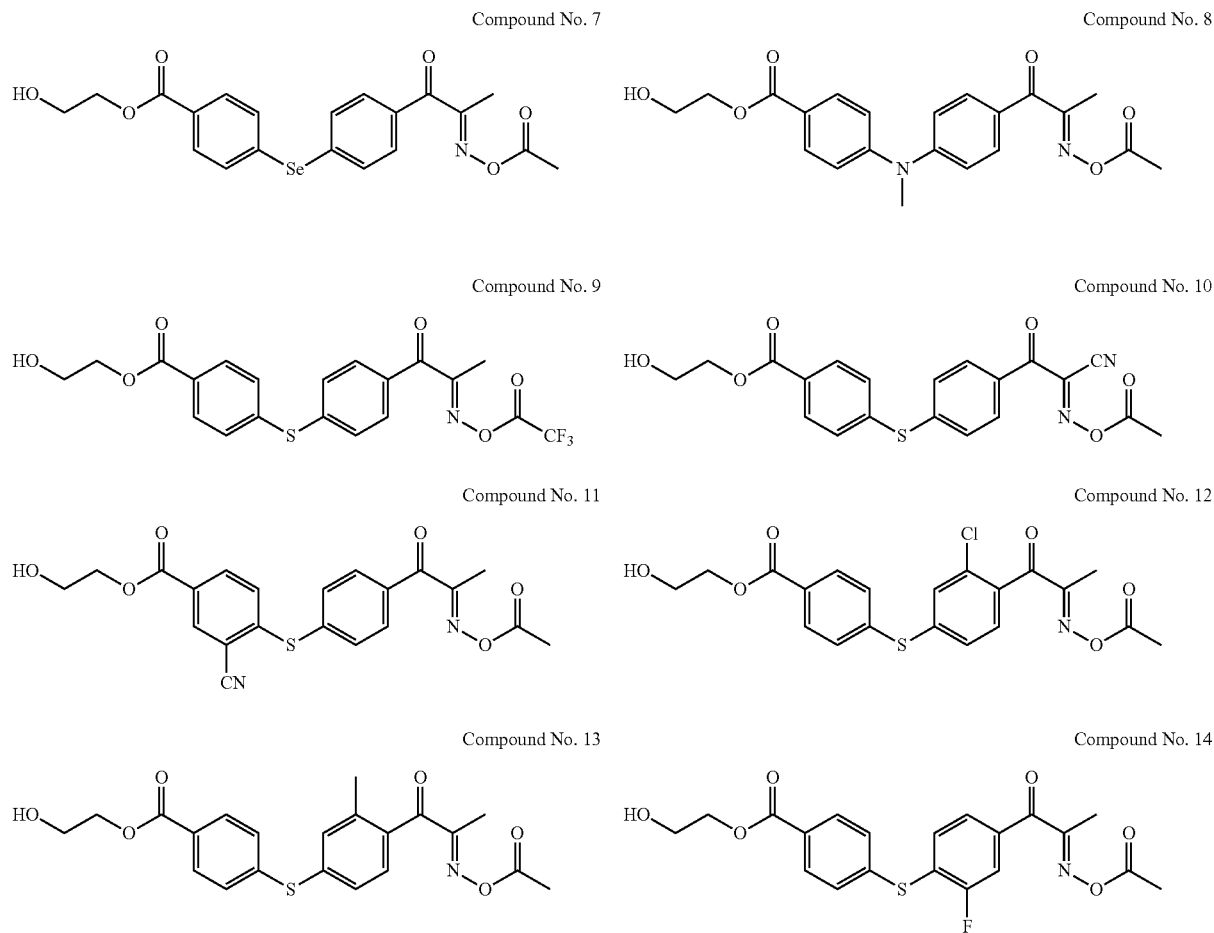

-continued
Compound No. 15
Compound No. 16
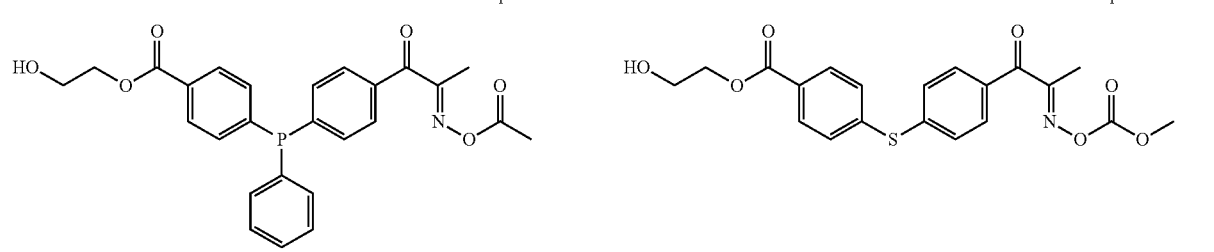
Compound No. 17
Compound No. 18
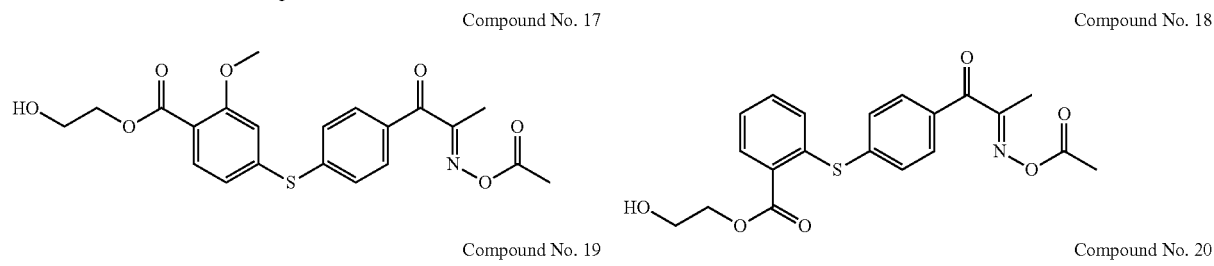
Compound No. 19
Compound No. 20
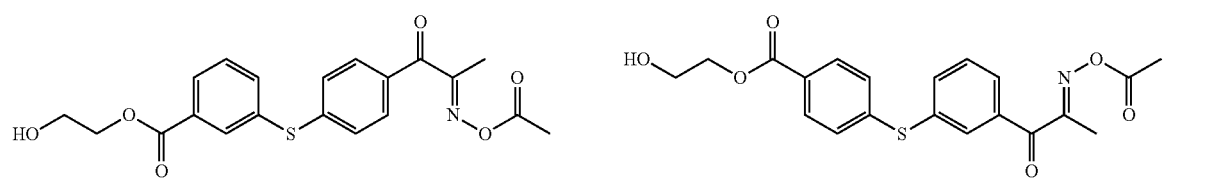
Compound No. 21
Compound No. 22
Compound No. 23
Compound No. 24
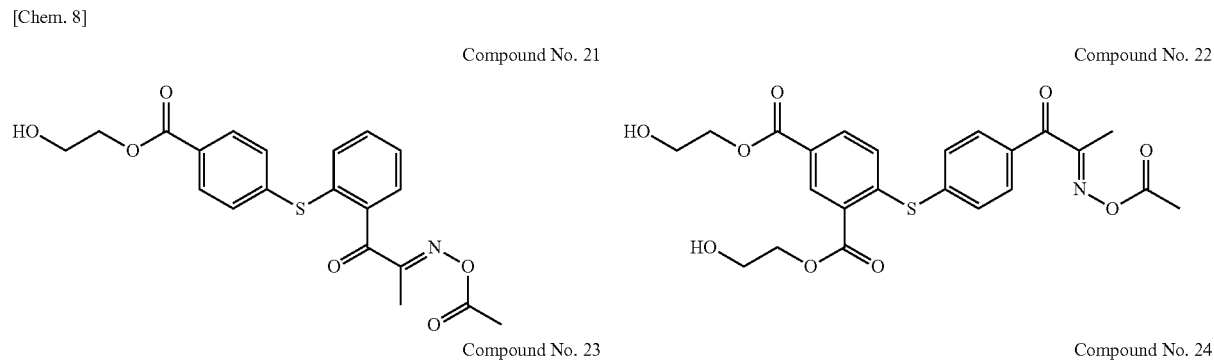
Compound No. 25
Compound No. 26
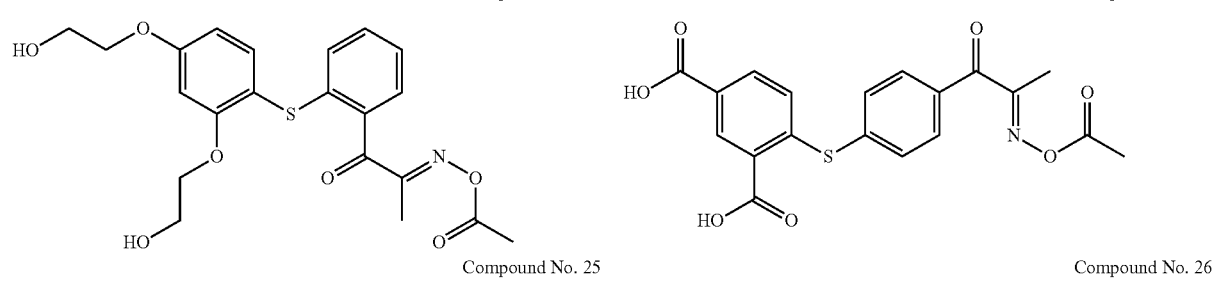
Compound No. 27
Compound No. 28
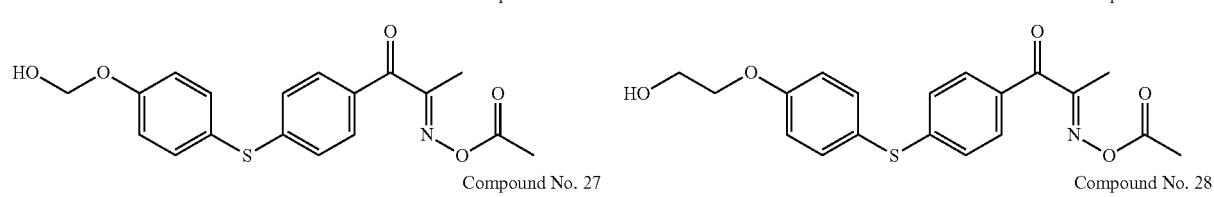
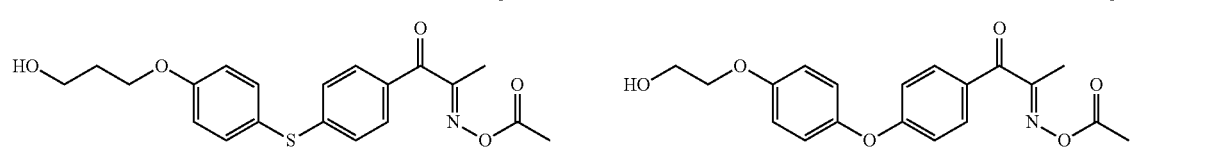

-continued
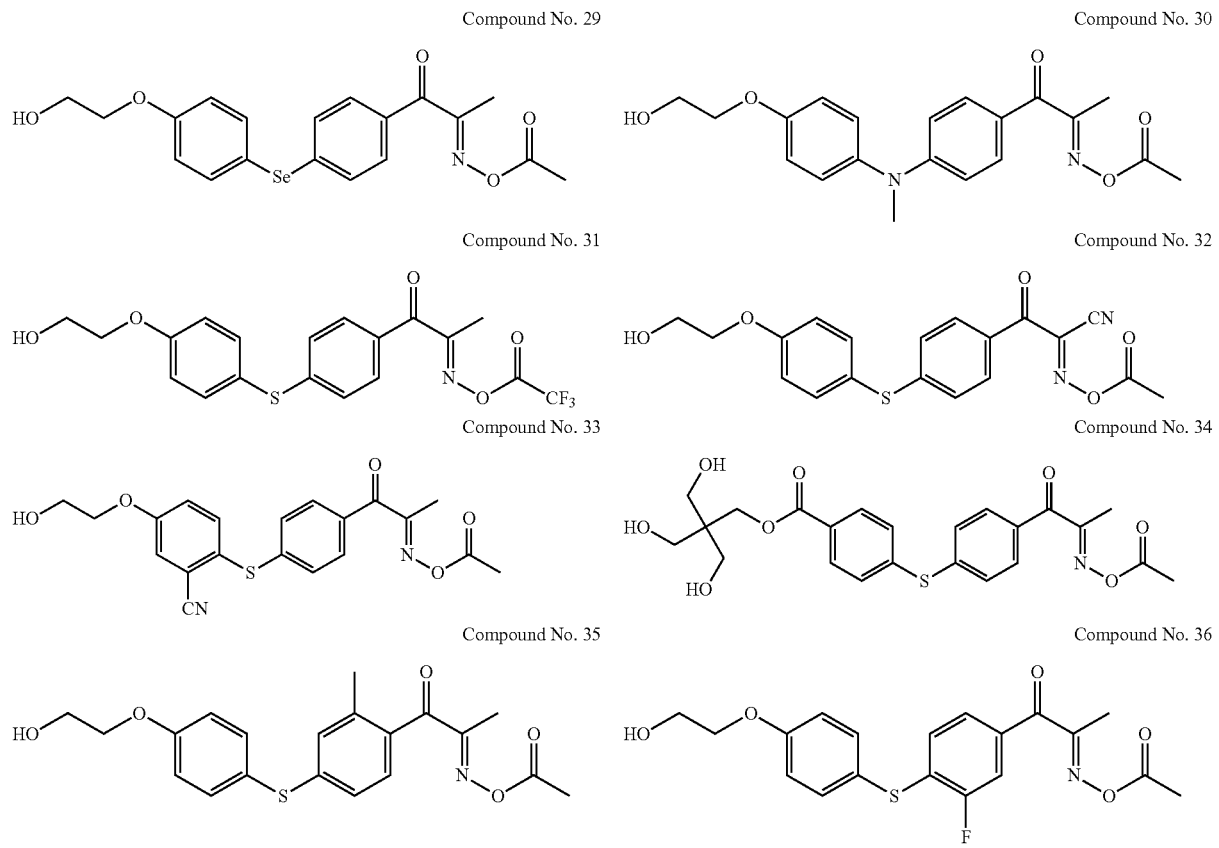
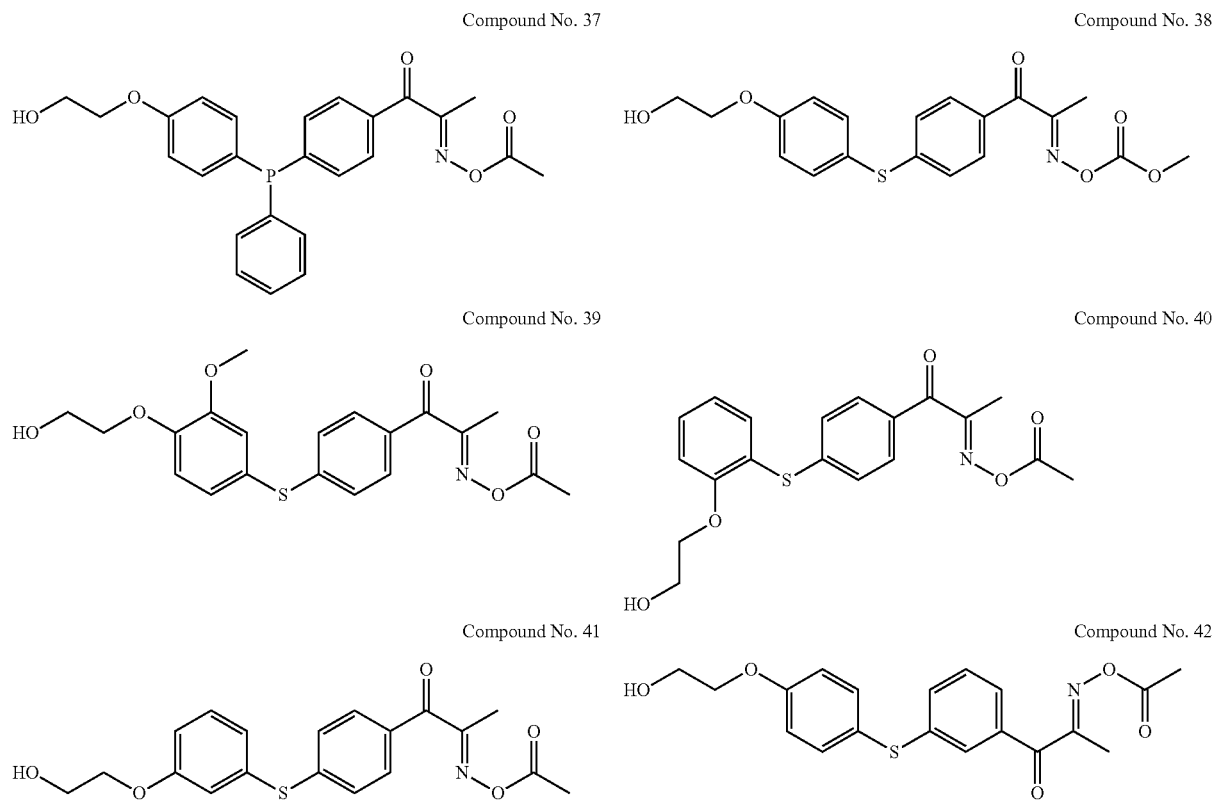

-continued
Compound No. 43
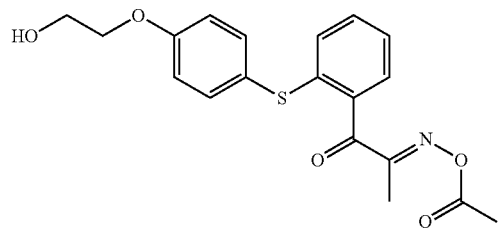
Compound No. 44
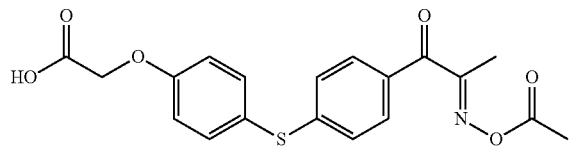
[Chem. 11]
Compound No. 45
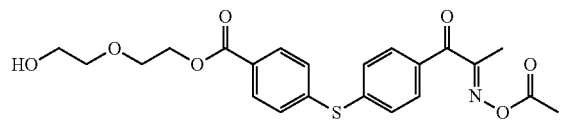
Compound No. 46
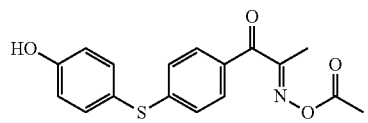
Compound No. 47
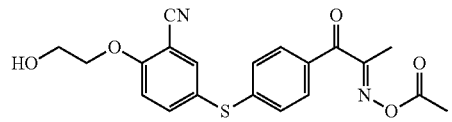
Compound No. 48
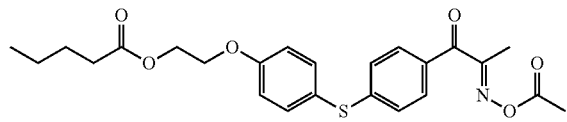
Compound No. 49
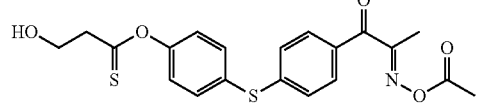
Compound No. 50
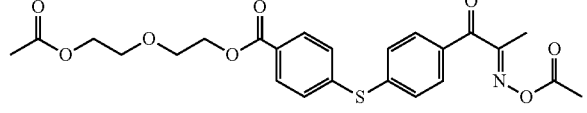
Compound No. 51
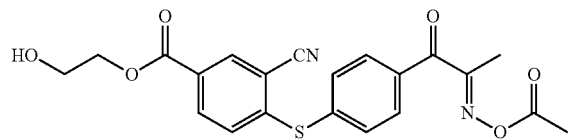
Compound No. 52
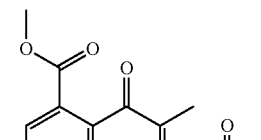
[Chem. 12]
Compound No. 53
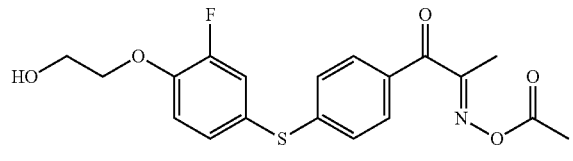
Compound No. 54
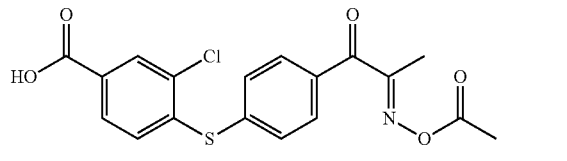
Compound No. 55
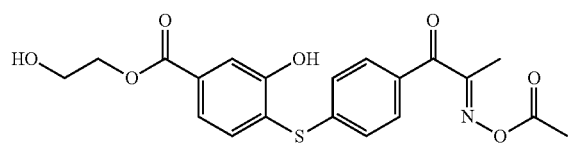
Compound No. 56
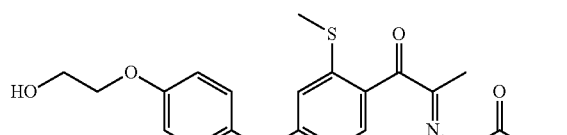
Compound No. 57
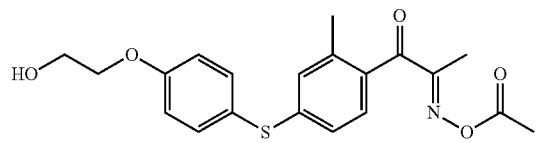
Compound No. 58
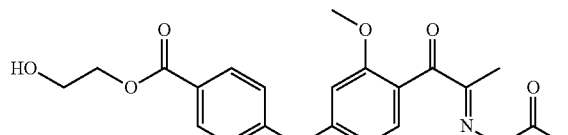

-continued
Compound No. 59
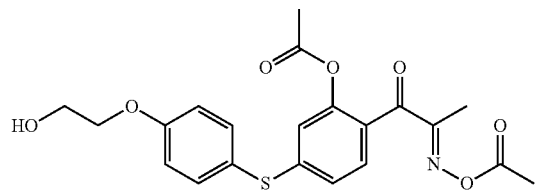
[Chem. 13]
Compound No. 60
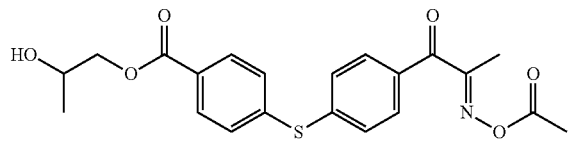
Compound No. 61
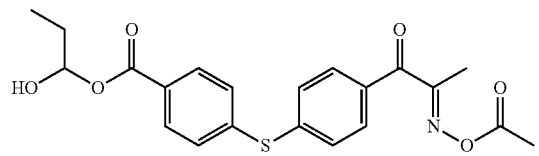
Compound No. 62
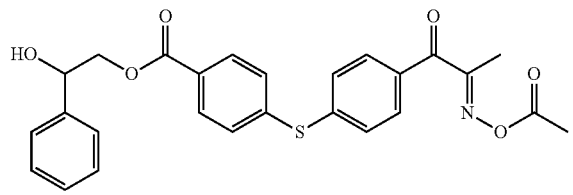
Compound No. 63
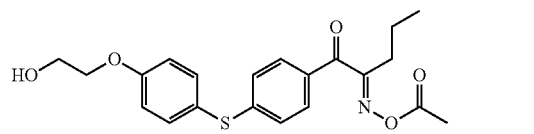
Compound No. 64
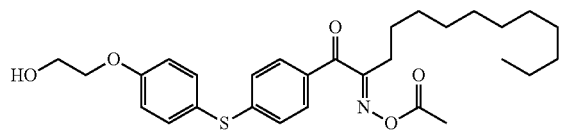
Compound No. 65
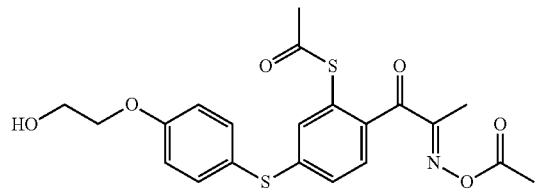
Compound No. 66
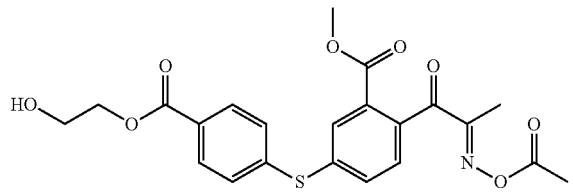
Compound No. 67
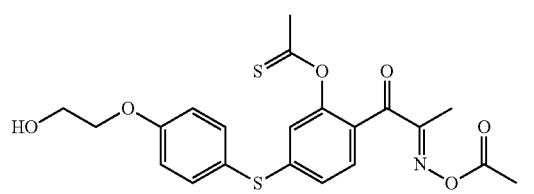
[Chem. 14]
Compound No. 68
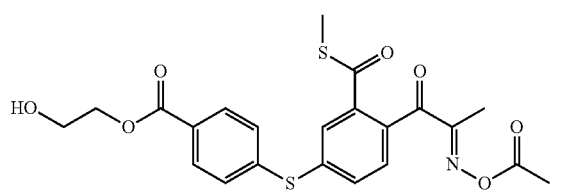
Compound No. 69
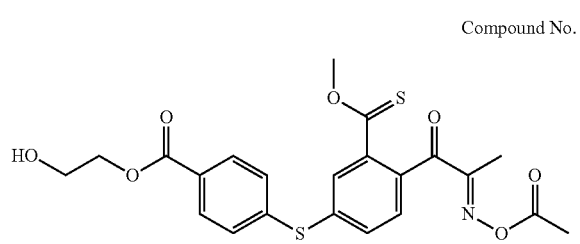
Compound No. 70
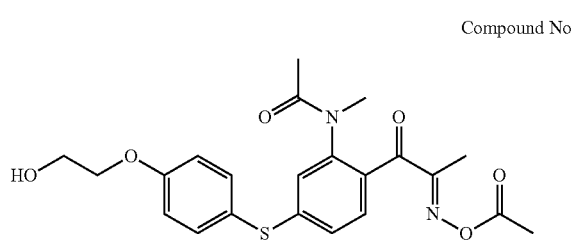
Compound No. 71
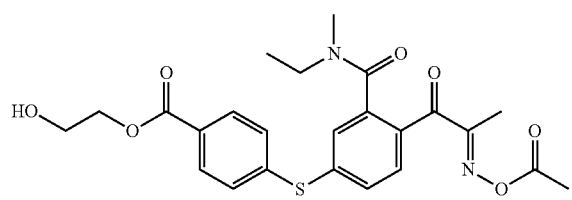
Compound No. 72
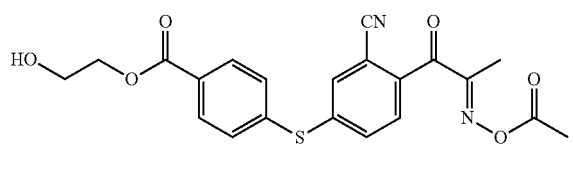

-continued
Compound No. 73  Compound No. 74
Compound No. 75  Compound No. 76
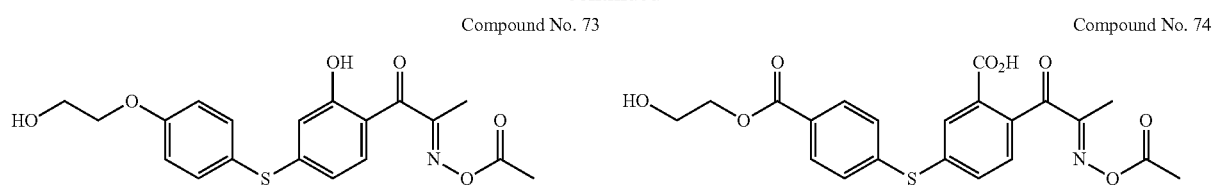
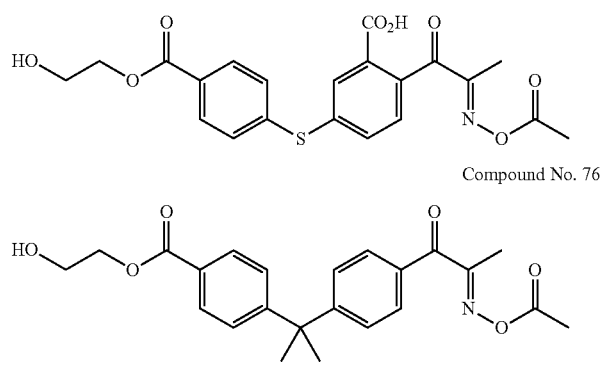
[Chem. 15]
Compound No. 77  Compound No. 78
Compound No. 79  Compound No. 80
Compound No. 81  Compound No. 82
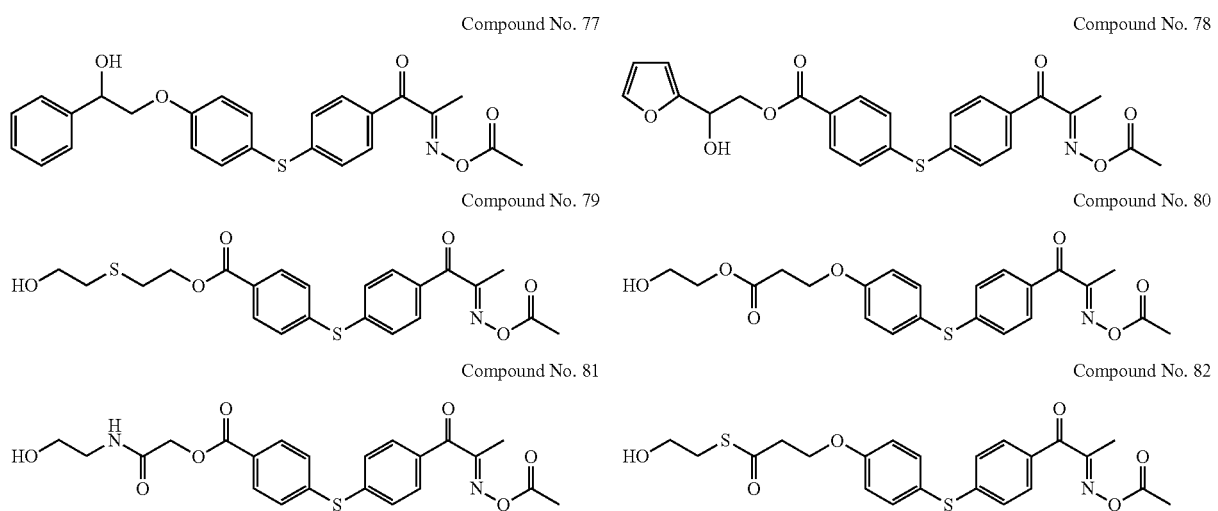
[Chem. 16]
Compound No. 83
Compound No. 84  Compound No. 85
Compound No. 86  Compound No. 87
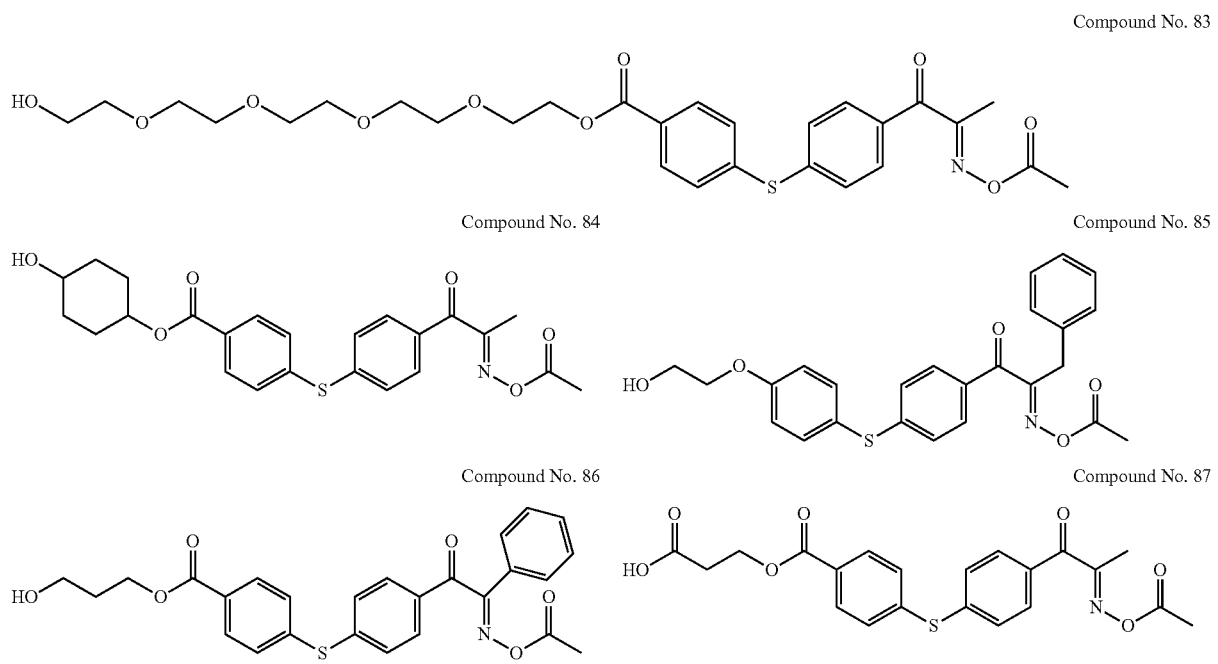

Compound No. 88

Compound No. 89

[Chem. 17]

Compound No. 90

Compound No. 91

Compound No. 92

Compound No. 93

Compound No. 94

Compound No. 95

Compound No. 96

Compound No. 97

[Chem. 18]

Compound No. 98

Compound No. 99

Compound No. 100

Compound No. 101

Compound No. 102

Compound No. 103

[Chem. 19]

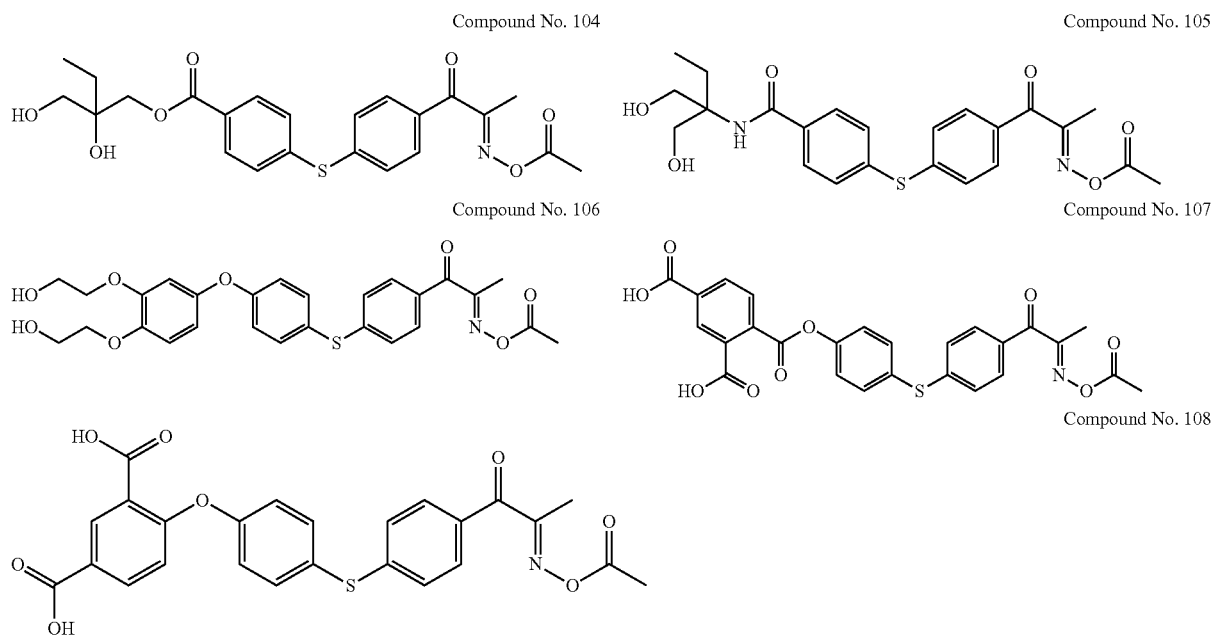

Compound No. 104
Compound No. 105
Compound No. 106
Compound No. 107
Compound No. 108

The oxime ester compound of the present invention represented by general formula (I) can be produced according to the process disclosed, for example, in JP-A-2000-80068 (U.S. Pat. No. 6,596,445), although not limited thereto. An example of a production process is described below in accordance with the equation shown in Chem. 20.

First, Ketone compound 1 is reacted with a nitrite ester in the presence of hydrochloric acid, to produce Oxime compound 2. The Oxime compound 2 is then reacted with Acid anhydride 3 or Acid chloride 3', to produce the oxime ester compound of the present invention represented by general formula (I). The following equation shows a sulfur atom as X in general formula (I), but compounds wherein X is an oxygen atom, a selenium atom, $CR^{41}R^{42}$, $NR^{43}$, or $PR^{44}$ can be produced according to the above process.

[Chem. 20]

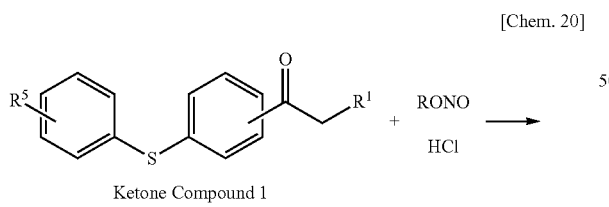

Ketone Compound 1

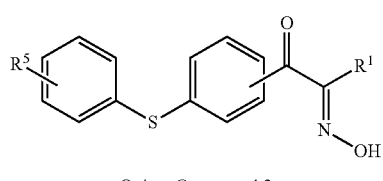

Oxime Compound 2

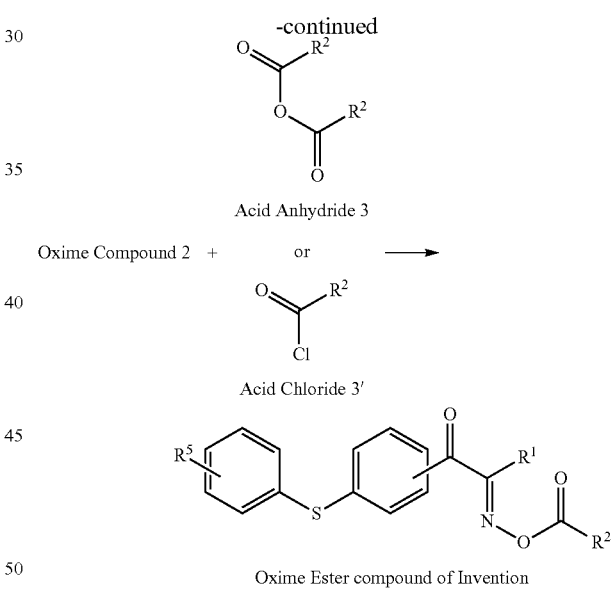

Acid Anhydride 3

Oxime Compound 2 + or

Acid Chloride 3'

Oxime Ester compound of Invention wherein, $R^1$, $R^2$, and $R^5$ are the same as those in general formula (I).

The novel oxime ester compound of the present invention described above is useful as a photopolymerization initiator.

The photopolymerization initiator of the present invention contains at least one type of oxime ester compound of the invention, and is particularly useful as a photopolymerization initiator for a polymerizable compound having an ethylenically unsaturated bond. The content of the present oxime ester compound is preferably 30 to 100% by mass, more preferably 50 to 100% by mass, with respect to the photopolymerization initiator of the present invention.

The photosensitive composition of the present invention contains, as essential components, the photopolymerization initiator of the present invention and a polymerizable compound having an ethylenically unsaturated bond, and also contains, in combination, optional components, such as an alkali-developable compound optionally having an ethylenically unsaturated group, an inorganic compound, a colorant, and a solvent.

Any ethylenically unsaturated polymerizable compound that has heretofore been used in photosensitive compositions can be used in the invention without particular limitation. Examples include: unsaturated aliphatic hydrocarbons, such as ethylene, propylene, butylene, isobutylene, vinyl chloride, vinylidene chloride, vinylidene fluoride, and tetrafluoroethylene; (meth)acrylic acid, α-chloroacrylic acid, itaconic acid, maleic acid, citraconic acid, fumaric acid, hymic acid, crotonic acid, isocrotonic acid, vinylacetic acid, allylacetic acid, cinnamic acid, sorbic acid, mesaconic acid, mono[2-(meth) acryloyloxyethyl]succinate, mono[2-(meth)acryloyloxyethyl]phthalate, a mono(methacrylate) of a polymer having a carboxy group and a hydroxyl group at both ends, such as ω-carboxypolycaprolactone mono(meth)acrylate; hydroxyethyl(meth)acrylate-maleate, hydroxypropyl(meth)acrylate-maleate, dicyclopentadiene-maleate, unsaturated polybasic acids such as a polyfunctional (meth)acrylate having one carboxyl group and two or more (meth)acryloyl groups; 2-hydroxyethyl(meth)acrylate, 2-hydroxypropyl(meth)acrylate, glycidyl(meth)acrylate, Compounds Nos. A1 to A4 shown below, methyl(meth)acrylate, butyl(meth)acrylate, isobutyl (meth)acrylate, t-butyl(meth)acrylate, cyclohexyl(meth) acrylate, n-octyl(meth)acrylate, isooctyl(meth)acrylate, isononyl(meth)acrylate, stearyl(meth)acrylate, lauryl(meth) acrylate, methoxyethyl(meth)acrylate, dimethylaminomethyl(meth)acrylate, dimethylaminoethyl(meth)acrylate, aminopropyl(meth)acrylate, dimethylaminopropyl(meth) acrylate, ethoxyethyl(meth)acrylate, poly(ethoxy)ethyl (meth)acrylate, butoxyethoxyethyl(meth)acrylate, ethylhexyl(meth)acrylate, phenoxyethyl(meth)acrylate, tetrahydrofuryl(meth)acrylate, vinyl(meth)acrylate, allyl(meth) acrylate, benzyl(meth)acrylate; esters between an unsaturated monobasic acid and a polyhydric alcohol or polyhydric phenol, such as ethylene glycol di(meth)acrylate, diethylene glycol di(meth)acrylate, triethylene glycol di(meth)acrylate, polyethylene glycol di(meth)acrylate, propylene glycol di(meth)acrylate, 1,4-butanediol di(meth)acrylate, 1,6-hexanediol di(meth)acrylate, trimethylolethane tri(meth)acrylate, trimethylolpropane tri(meth)acrylate, dipentaerythritol hexa(meth)acrylate, dipentaerythritol penta(meth)acrylate, pentaerythritol tetra(meth)acrylate, pentaerythritol tri(meth) acrylate, tricyclodecanedimethylol di(meth)acrylate, tri [(meth)acryloylethyl]isocyanurate, and polyester(meth) acrylate oligomers; metal salts of unsaturated polybasic acids, such as zinc(meth)acrylate and magnesium(meth)acrylate; unsaturated polybasic acid anhydrides, such as maleic anhydride, itaconic anhydride, citraconic anhydride, methyltetrahydrophthalic anhydride, tetrahydrophthalic anhydride, trialkyltetrahydrophthalic anhydrides, 5-(2,5-dioxotetrahydrofuryl)-3-methyl-3-cyclohexene-1,2-dicarboxylic acid anhydride, trialkyltetrahydrophthalic anhydride-maleic anhydride adducts, dodecenylsuccinic anhydride, and methylhymic anhydride; amides formed between an unsaturated monobasic acid and a polyfunctional amine, such as (meth) acrylamide, methylenebis(meth)acrylamide, diethylenetriaminetris(meth)acrylamide, xylylenebis(meth)acrylamide, α-chloroacrylamide, and N-2-hydroxyethyl(meth)acrylamide; unsaturated aldehydes, such as acrolein; unsaturated nitriles, such as (meth)acrylonitrile, α-chloroacrylonitrile, vinylidene cyanide, and allyl cyanide; unsaturated aromatic compounds, such as styrene, 4-methylstyrene, 4-ethylstyrene, 4-methoxystyrene, 4-hydroxystyrene, 4-chlorostyrene, divinylbenzene, vinyltoluene, vinylbenzoic acid, vinylphenol, vinylsulfonic acid, 4-vinylbenzenesulfonic acid, vinylbenzyl methyl ether, and vinylbenzyl glycidyl ether; unsaturated ketones, such as methyl vinyl ketone; unsaturated amine compounds, such as vinylamine, allylamine, N-vinylpyrrolidone, and vinylpiperidine; vinyl alcohols, such as allyl alcohol and crotyl alcohol; vinyl ethers, such as vinyl methyl ether, vinyl ethyl ether, n-butyl vinyl ether, isobutyl vinyl ether, and allyl glycidyl ether; unsaturated imides, such as maleimide, N-phenylmaleimide, and N-cyclohexylmaleimide; indenes, such as indene and 1-methylindene; aliphatic conjugated dienes, such as 1,3-butadiene, isoprene, and chloroprene; macromonomers having a mono(meth)acryloyl group at the end of the polymeric molecular chain thereof, such as polystyrene, polymethyl(meth)acrylate, poly-n-butyl (meth)acrylate, and polysiloxanes; vinyl chloride, vinylidene chloride, divinyl succinate, diallyl phthalate, triallyl phosphate, triallyl isocyanurate, vinyl thioether, vinylimidazole, vinyloxazoline, vinylcarbazole, vinylpyrrolidone, vinylpyridine, vinylurethane compounds formed between a hydroxyl-containing vinyl monomer and a polyisocyanate compound, and vinylepoxy compounds formed between a hydroxyl-containing vinyl monomer and a polyepoxy compound.

Of these ethylenically unsaturated polymerizable compounds, the oxime-ester-compound-containing photopolymerization initiator of the present invention is suitable for a mono(meth)acrylate of a polymer having a carboxy group and a hydroxyl group at respective ends, a polyfunctional (meth)acrylate having one carboxy group and two or more (meth)acryloyl groups, and an ester between an unsaturated monobasic acid and a polyhydric alcohol or polyhydric phenol.

The polymerizable compounds may be used either individually or as a mixture containing two or more thereof. Where two or more compounds are to be used in combination, they may be copolymerized in advance to form a copolymer.

[Chem. 21]

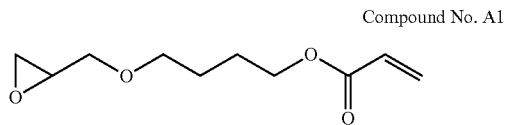

Compound No. A1

[Chem. 22]

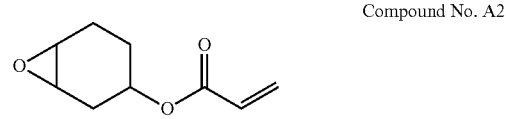

Compound No. A2

[Chem. 23]

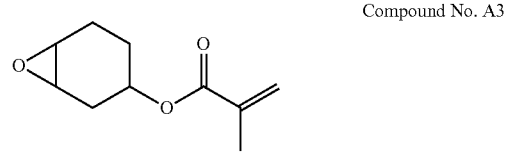

Compound No. A3

[Chem. 24]

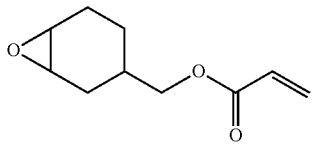

Compound No. A4

The alkali-developable compound optionally having an ethylenically unsaturated group is not particularly limited as long as it is soluble in an alkaline aqueous solution, and examples include resins etc. disclosed, for example, in JP-A-2004-264414.

Examples of resins that may be used as the alkali-developable compound optionally having an ethylenically unsaturated group include: acrylic ester copolymers; phenol and/or cresol novolac epoxy resins; polyphenylmethane epoxy resins having polyfunctional epoxy groups; epoxy acrylate resins; and resins obtained by reacting an epoxy compound, such as the epoxy compound represented by the following general formula (IV), with an unsaturated monobasic acid followed by reaction with a polybasic acid anhydride.

Preferred among the above are the resins obtained by reacting an epoxy compound, such as the epoxy compound represented by the following general formula (IV), with an unsaturated monobasic acid followed by reaction with a polybasic acid anhydride.

It is also preferable that the alkali-developable compound optionally having an ethylenically unsaturated bond contains 0.2 to 1.0 equivalents of unsaturated groups.

[Chem. 25]

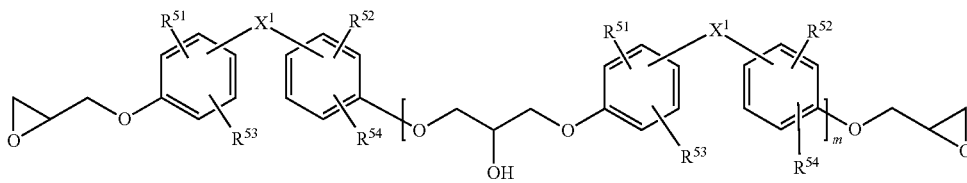

(IV)

wherein, $X^1$ represents a direct bond, a methylene group, a $C_{1-4}$ alkylidene group, a $C_{3-20}$ alicyclic hydrocarbon group, O, S, $SO_2$, SS, SO, CO, OCO, or a substituent represented by the following Chem. 26, Chem. 27, or Chem. 28; the alkylidene group may optionally be substituted by a halogen atom; $R^{51}$, $R^{52}$, $R^{53}$, and $R^{54}$ each independently represent a hydrogen atom, a $C_{1-5}$ alkyl group, a $C_{1-8}$ alkoxy group, a $C_{2-5}$ alkenyl group, or a halogen atom; the alkyl group, the alkoxy group, and the alkenyl group may optionally be substituted by a halogen atom; m is an integer of 0 to 10; and where m is not 0, any optical isomer may do.)

[Chem. 26]

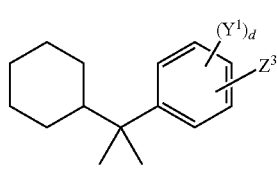

wherein, $Z^3$ represents a hydrogen atom, a phenyl group optionally substituted by a $C_{1-10}$ alkyl group or a $C_{1-10}$ alkoxy group, or a $C_{3-10}$ cycloalkyl group optionally substituted by a $C_{1-10}$ alkyl group or a $C_{1-10}$ alkoxy group; $Y^1$ represents a $C_{1-10}$ alkyl group, a $C_{1-10}$ alkoxy group, a $C_{2-10}$ alkenyl group, or a halogen atom; the alkyl group, the alkoxy group, and the alkenyl group may optionally be substituted by a halogen atom; and d is an integer of 0 to 5.

[Chem. 27]

[Chem. 28]

wherein, $Y^2$ and $Z^4$ each independently represent a $C_{1-10}$ alkyl group optionally substituted by a halogen atom, a $C_{6-20}$ aryl group optionally substituted by a halogen atom, a $C_{6-20}$ aryloxy group optionally substituted by a halogen atom, a $C_{6-20}$ arylthio group optionally substituted by a halogen atom, a $C_{6-20}$ arylalkenyl group optionally substituted by a halogen atom, a $C_{7-20}$ arylalkyl group optionally substituted by a halogen atom, a $C_{2-20}$ heterocyclic group optionally substituted by a halogen atom, or a halogen atom; the alkylene portion in the alkyl group and the arylalkyl group may be interrupted by an unsaturated bond, —O—, or —S—; $Z^4$ may form a ring with an adjacent $Z^4$; p is an integer of 0 to 4; q is an integer of 0 to 8; r is an integer of 0 to 4; s is an integer of 0 to 4; and the sum of r and s is an integer of 2 to 4.

Examples of the unsaturated monobasic acid for reaction with the epoxy compound include acrylic acid, methacrylic acid, crotonic acid, cinnamic acid, sorbic acid, hydroxyethyl methacrylate-maleate, hydroxyethyl acrylate-maleate, hydroxypropyl methacrylate-maleate, hydroxypropyl acrylate-maleate, and dicyclopentadiene-maleate.

Examples of the polybasic acid anhydride for reaction with the reaction product after the reaction of the unsaturated monobasic acid include biphenyltetracarboxylic acid dianhydride, tetrahydrophthalic anhydride, succinic anhydride, biphthalic anhydride, maleic anhydride, trimellitic anhydride, pyromellitic anhydride, 2,2',3,3'-benzophenonetetracarboxylic acid anhydride, ethylene glycol bisanhydrotrimellitate, glycerol trisanhydrotrimellitate, hexahydrophthalic anhydride, methyltetrahydrophthalic anhydride, nadic anhydride, methylnadic anhydride, trialkyltetrahydrophthalic anhydrides, hexahydrophthalic anhydride, 5-(2,5-dioxotetrahydrofuryl)-3-methyl-3-cyclohexene-1,2-dicarboxylic acid anhydride, trialkyltetrahydrophthalic anhydride-maleic acid anhydride adducts, dodecenylsuccinic anhydride, and methylhymic anhydride.

Preferably, the molar ratio on reaction among the epoxy compound, the unsaturated monobasic acid, and the polybasic acid anhydride is as follows.

An epoxy adduct formed by reacting the epoxy compound and the unsaturated monobasic acid preferably has a structure wherein 0.1 to 1.0 carboxyl group of the unsaturated monobasic acid is added per one epoxy group of the epoxy compound. The polybasic acid anhydride is used in such a molar ratio as to preferably provide 0.1 to 1.0 acid anhydride structure per one hydroxyl group of the above epoxy adduct.

The reactions among the epoxy compound, the unsaturated monobasic acid, and the polybasic acid anhydride can be carried out according to usual methods.

The alkali-developable photosensitive resin composition of the present invention, which is an embodiment of the photosensitive composition of the invention, contains, as essential components, the photopolymerization initiator of the invention, the polymerizable compound having an ethylenically unsaturated bond, and the alkali-developable compound optionally having an ethylenically unsaturated group, and also contains, in combination, optional components, such as an inorganic compound, a colorant, and a solvent. Note that an alkali-developable photosensitive resin composition of the invention containing a colorant is also referred to particularly as an "alkali-developable, colored photosensitive resin composition" of the invention.

The above-described polymerizable compound having an ethylenically unsaturated bond and the alkali-developable compound optionally having an ethylenically unsaturated group may be the same compound or may be different compounds, and they may be used either individually or as a mixture containing two or more thereof.

In order to improve the developability of the alkali-developable (colored) photosensitive resin composition of the invention, the acid value may be adjusted using a mono- or polyfunctional epoxy compound in combination with the above-described alkali-developable compound optionally having an ethylenically unsaturated bond. It is preferable that the acid value of the solids content of the above-described alkali-developable compound optionally having an ethylenically unsaturated bond is within a range of 5 to 120 mg-KOH/g, and accordingly, the amount of the mono- or polyfunctional epoxy compound to be used is preferably determined so as to satisfy the above acid value range.

Examples of the monofunctional epoxy compound include glycidyl methacrylate, methyl glycidyl ether, ethyl glycidyl ether, propyl glycidyl ether, isopropyl glycidyl ether, butyl glycidyl ether, isobutyl glycidyl ether, t-butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, 2-ethylhexyl glycidyl ether, allyl glycidyl ether, propargyl glycidyl ether, p-methoxyethyl glycidyl ether, phenyl glycidyl ether, p-methoxy glycidyl ether, p-butylphenyl glycidyl ether, cresyl glycidyl ether, 2-methylcresyl glycidyl ether, 4-nonylphenyl glycidyl ether, benzyl glycidyl ether, p-cumylphenyl glycidyl ether, trityl glycidyl ether, 2,3-epoxypropyl methacrylate, epoxidized soybean oil, epoxidized linseed oil, glycidyl butyrate, vinylcyclohexane monoxide, 1,2-epoxy-4-vinylcyclohexane, styrene oxide, pinene oxide, methylstyrene oxide, cyclohexene oxide, propylene oxide, and Compounds Nos. E1 and E2 below.

[Chem. 29]

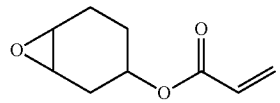

Compound No. E1

[Chem. 30]

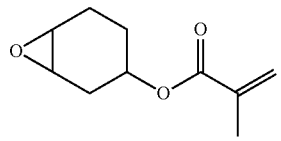

Compound No. E2

It is preferable to use at least one compound selected from a group consisting of bisphenol epoxy compounds and glycidyl ethers as the polyfunctional epoxy compound, because this allows to provide an alkali-developable (colored) photosensitive resin composition having further improved characteristics. Examples of usable bisphenol epoxy compounds include the epoxy compounds represented by general formula (IV) and other bisphenol epoxy compounds, such as hydrogenated bisphenol epoxy compounds.

Examples of usable glycidyl ethers include ethylene glycol diglycidyl ether, propylene glycol diglycidyl ether, 1,4-butanediol diglycidyl ether, 1,6-hexanediol diglycidyl ether, 1,8-octanediol diglycidyl ether, 1,10-decanediol diglycidyl ether, 2,2-dimethyl-1,3-propanediol diglycidyl ether, diethylene glycol diglycidyl ether, triethylene glycol diglycidyl ether, tetraethylene glycol diglycidyl ether, hexaethylene glycol diglycidyl ether, 1,4-cyclohexanedimethanol diglycidyl ether, 1,1,1-tri(glycidyloxymethyl)propane, 1,1,1-tri(glycidyloxymethyl)ethane, 1,1,1-tri(glycidyloxymethyl)methane, and 1,1,1,1-tetra(glycidyloxymethyl)methane.

Other usable polyfunctional epoxy compounds include: novolac epoxy compounds, such as phenol novolac epoxy compounds, biphenyl novolac epoxy compounds, cresol novolac epoxy compounds, bisphenol A novolac epoxy compounds, and dicyclopentadiene novolac epoxy compounds; alicyclic epoxy compounds, such as 3,4-epoxy-6-methylcyclohexylmethyl-3,4-epoxy-6-methylcyclohexanecarboxylate, 3,4-epoxycyclohexylmethyl-3,4-epoxycyclohexanecarboxylate, and 1-epoxyethyl-3,4-epoxycyclohexane; glycidyl esters, such as diglycidyl phthalate, diglycidyl tetrahydrophthalate, and glycidyl dimerate; glycidylamines, such as tetraglycidyl diaminodiphenylmethane, triglycidyl p-aminophenol, and N,N-diglycidylaniline; heterocyclic epoxy compounds, such as 1,3-diglycidyl-5,5-dimethylhydantoin and triglycidyl isocyanurate; dioxide compounds, such as dicyclopentadiene dioxide; naphthalene epoxy compounds; triphenylmethane epoxy compounds; and dicyclopentadiene epoxy compounds.

In the photosensitive composition of the present invention, the content of the present photopolymerization initiator is not particularly limited, but is preferably 1 to 70 parts by mass, more preferably 1 to 50 parts by mass, even more preferably 5 to 30 parts by mass, with respect to 100 parts by mass of the polymerizable compound having an ethylenically unsaturated bond.

Particularly in cases where the photosensitive composition of the invention is an alkali-developable (colored) photosensitive resin composition, the content of the alkali-developable compound optionally having an ethylenically unsaturated bond is preferably 1 to 20% by mass, more preferably 3 to 12% by mass, with respect to the alkali-developable (colored) photosensitive resin composition of the invention.

The photosensitive composition of the invention may optionally contain a solvent. Usually, solvents capable of dissolving or dispersing the above-described components (such as the photopolymerization initiator of the invention, the polymerizable compound having an ethylenically unsaturated bond, etc.) are used where necessary. Examples of such solvents include: ketones, such as methyl ethyl ketone, methyl amyl ketone, diethyl ketone, acetone, methyl isopropyl ketone, methyl isobutyl ketone, cyclohexanone, and 2-heptanone; ethers, such as ethyl ether, dioxane, tetrahydrofuran, 1,2-dimethoxyethane, 1,2-diethoxyethane, and dipropylene glycol dimethyl ether; esters, such as methyl acetate, ethyl acetate, n-propyl acetate, isopropyl acetate, n-butyl acetate, cyclohexyl acetate, ethyl lactate, dimethyl succinate, and Texanol; cellosolve-type solvents, such as ethylene glycol monomethyl ether and ethylene glycol monoethyl ether; alcohols, such as methanol, ethanol, iso- or n-propanol, iso- or n-butanol, and amyl alcohol; ether esters, such as ethylene glycol monomethyl acetate, ethylene glycol monoethyl acetate, propylene glycol-1-monomethyl ether-2-acetate, dipropylene glycol monomethyl ether acetate, 3-methoxybutyl acetate, and ethoxyethyl propionate; BTX solvents, such as benzene, toluene, xylene, etc.; aliphatic hydrocarbons, such as hexane, heptane, octane, and cyclohexane; terpene hydrocarbon oils, such as turpentine oil, D-limonene, and pinene; paraffinic solvents, such as mineral spirit, Swasol #310 (available from Cosmo Matsuyama Oil Co., ltd.), and Solvesso #100 (available from Exxon Chemical); halogenated aliphatic hydrocarbons, such as carbon tetrachloride, chloroform, trichloroethylene, methylene chloride, and 1,2-dichloroethane; halogenated aromatic hydrocarbons, such as chlorobenzene; carbitol solvents; aniline; triethylamine; pyridine; acetic acid; acetonitrile; carbon disulfide; N,N-dimethylformamide; N,N-dimethylacetamide; N-methylpyrrolidone; dimethyl sulfoxide; and water. These solvents may be used either individually or as a mixed solvent containing two or more thereof.

Among the above, solvents such as ketones and ether esters, and particularly propylene glycol-1-monomethyl ether-2-acetate, cyclohexanone, etc., are preferred because of their good compatibility with resists and photopolymerization initiators in the photosensitive composition.

The photosensitive composition of the invention (especially the alkali-developable photosensitive resin composition) may further contain a colorant to be formulated into a colored (alkali-developable) photosensitive composition. Examples of the colorant include pigments, dyes, and naturally-occurring colorants. The colorants may be used either individually or as a mixture containing two or more thereof.

Organic or inorganic pigments may be used, and examples include: nitroso compounds; nitro compounds; azo compounds; diazo compounds; xanthene compounds; quinoline compounds; anthraquinone compounds; coumarin compounds; phthalocyanine compounds; isoindolinone compounds; isoindoline compounds; quinacridone compounds; anthanthrone compounds; perynone compounds; perylene compounds; diketopyrrolopyrrole compounds; thioindigo compounds; dioxazine compounds; triphenylmethane compounds; quinophthalone compounds; naphthalenetetracarboxylic acids; metal complex compounds, such as azo dyes and cyanine dyes; lake pigments; carbon black species produced by the furnace, channel, or thermal process, and other carbon black species, such as acetylene black, Ketjen black, and lamp black; the above-mentioned carbon black adjusted or covered with an epoxy resin, the above-mentioned carbon black dispersed in advance with a resin in a solvent so as to adsorb 20 to 200 mg/g of the resin, the above-mentioned carbon black surface-treated with an acid or an alkali, the above-mentioned carbon black having an average particle size of 8 nm or above and a DBP oil absorption of 90 ml/100 g or less, and the above-described carbon black whose total oxygen amount derived from the amount of CO and $CO_2$ in the volatilized substances at 950° C. is 9 mg or more per 100 $m^2$ of the carbon black's surface area; graphite, graphitized carbon black, activated carbon, carbon fiber, carbon nanotube, carbon microcoil, carbon nanohorn, carbon aerogel, fullerene; aniline black, pigment black 7, titanium black; chromium oxide green, Milori blue, cobalt green, cobalt blue, manganese compounds, ferrocyanides, phosphate ultramarine blue, Prussian blue, ultramarine, cerulean blue, viridian, emerald green, lead sulfate, lead yellow, zinc yellow, Bengal red (red iron (III) oxide), cadmium red, synthetic iron black, and amber. The pigments may be used either individually or as a mixture thereof.

Commercially-available pigments may be used, and examples include: pigment red 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, and 254; pigment orange 13, 31, 34, 36, 38, 43, 46, 48, 49, 51, 52, 55, 59, 60, 61, 62, 64, 65, and 71; pigment yellow 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; pigment green 7, 10, and 36; pigment blue 15, 15:1, 15:2, 15:3, 15:4, 15:5, 15:6, 22, 24, 56, 60, 61, 62, and 64; and pigment violet 1, 19, 23, 27, 29, 30, 32, 37, 40, and 50.

Examples of the dyes include azo dyes, anthraquinone dyes, indigoid dyes, triarylmethane dyes, xanthene dyes, alizarine dyes, acridine dyes, stilbene dyes, thiazole dyes, naphthol dyes, quinoline dyes, nitro dyes, indamine dyes, oxazine dyes, phthalocyanine dyes, and cyanine dyes. Several dyes may be used as a mixture.

In the photosensitive composition of the invention, the colorant content is preferably 50 to 350 parts by mass, more preferably 100 to 250 parts by mass, with respect to 100 parts by mass of the polymerizable compound having an ethylenically unsaturated bond.

The photosensitive composition of the invention may further contain an inorganic compound. Examples of the inorganic compound include: metal oxides, such as nickel oxide, iron oxide, iridium oxide, titanium oxide, zinc oxide, magnesium oxide, calcium oxide, potassium oxide, silica, and alumina; layered clay minerals, Milori blue, calcium carbonate, magnesium carbonate, cobalt compounds, manganese compounds, glass powder (especially glass frit), mica, talc, kaolin, ferrocyanides, various metal sulfates, sulfides, selenides, aluminum silicate, calcium silicate, aluminum hydroxide, platinum, gold, silver, and copper.

Preferred among the above are, for example, glass frit, titanium oxide, silica, layered clay minerals, and silver. In the photosensitive composition of the invention, the inorganic compound content is preferably 0.1 to 1000 parts by mass, more preferably 10 to 800 parts by mass, with respect to 100 parts by mass of the polymerizable compound having an ethylenically unsaturated bond. Note that the inorganic compounds may be used singly or two or more may be used in combination.

The inorganic compounds are used as, for example, fillers, antireflection agents, electrically-conductive agents, stabilizers, flame retardants, mechanical strength improving agents, specific wavelength absorbing agents, or ink repellent agents.

The photosensitive composition of the invention may also contain a dispersing agent for dispersing the colorant and/or the inorganic compound. Any dispersing agent may be used without limitation as long as it can disperse and stabilize the colorant or the inorganic compound, and commercially-available dispersing agents, such as the BYK series available from BYK-Chemie, may be used. Particularly preferred are polymeric dispersing agents composed of polyester, polyether, or polyurethane having a basic functional group, and dispersing agents having a nitrogen-atom-containing basic functional group and wherein the nitrogen-containing functional group is an amine and/or its quaternary salt and the amine value is 1 to 100 mg-KOH/g.

The photosensitive composition of the present invention may contain other photopolymerization initiators in combination with the oxime ester compound of the invention. Various known compounds may be used as the other photopolymerization initiator(s), and examples include: benzophenone, phenyl biphenyl ketone, 1-hydroxy-1-benzoylcyclohexane, benzoin, benzyl dimethyl ketal, 1-benzyl-1-dimethylamino-1-(4'-morpholinobenzoyl)propane, 2-morpholyl-2-(4'-methylmercapto)benzoylpropane, thioxanthone, 1-chloro-4-propoxythioxanthone, isopropylthioxanthone, diethylthioxanthone, ethylanthraquinone, 4-benzoyl-4'-methyldiphenyl sulfide, benzoin butyl ether, 2-hydroxy-2-benzoylpropane, 2-hydroxy-2-(4'-isopropyl)benzoylpropane, 4-butylbenzoyltrichloromethane, 4-phenoxybenzoyldichloromethane, methyl benzoylformate, 1,7-bis(9'-acridinyl) heptane, 9-n-butyl-3,6-bis(2'-morpholinoisobutyroyl)carbazole, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, 2,2-bis(2-chlorophenyl)-4,5,4',5'-tetraphenyl-1,2'-biimidazole, 4,4-azobisisobutyronitrile, triphenylphosphine, camphorquinone; N-1414, N-1717, N-1919, and PZ-408 (from ADEKA Corp.); Irgacure 369, Irgacure 907, Irgacure OXE 01, and Irgacure OXE 02 (from Ciba Specialties Chemicals Corp.); benzoyl peroxide, and compounds represented by the following general formulas (V) to (VII). The amount of the other photopolymerization initiator(s), if used, is preferably equal to or less than 1 time, by mass, the amount of the oxime ester compound used in the invention. These photopolymerization initiators may be used singly or two or more may be used in combination.

[Chem. 31]

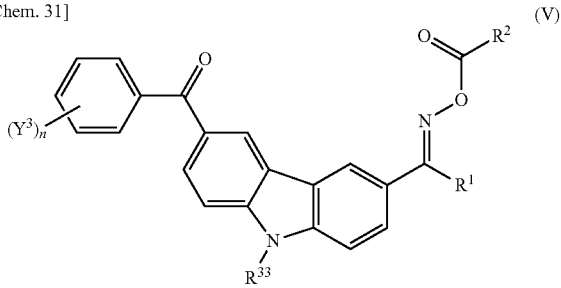

(V)

wherein, $R^1$, $R^2$, and $R^{33}$ are the same as those in general formula (I); $Y^3$ represents a halogen atom or an alkyl group; and n is an integer of 0 to 5.

[Chem. 32]

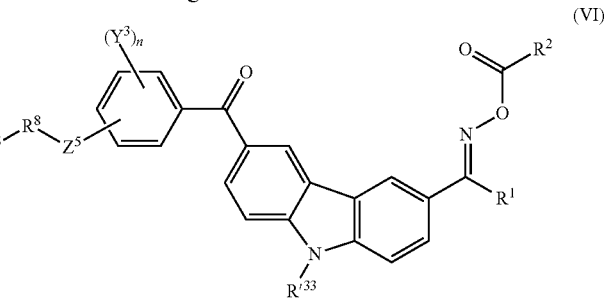

(VI)

wherein, $R^1$, $R^2$, and $R^{33}$ are the same as those in general formula (I); $Y^3$ and n are the same as those in general formula (V); $R'^1$ and $R'^2$ are the same as $R^1$; $R'^{33}$ is the same as $R^{33}$; $Y'^3$ is the same as $Y^3$; $R^8$ represents a diol residue or a dithiol residue; and $Z^5$ represents an oxygen atom or a sulfur atom.

[Chem. 33]

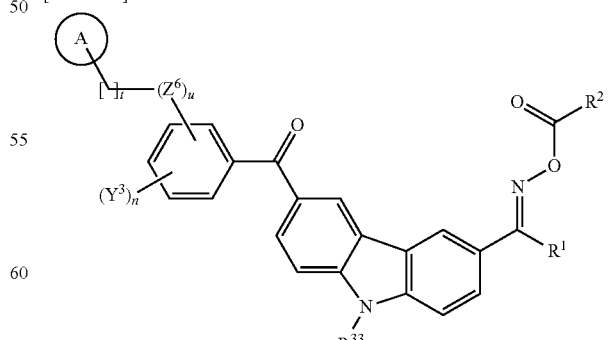

(VII)

wherein, $R^1$, $R^2$, and $R^{33}$ are the same as those in general formula (I); $Y^3$ and n are the same as those in general formula (V); $Z^6$ represents an oxygen atom, a sulfur atom, or a selenium atom; A represents a heterocyclic group; t is an integer of 0 to 5; and u is 0 or 1.

The photosensitive composition of the present invention may further contain, as necessary, commonly-used additives, including, for example: thermal polymerization inhibitors, such as p-anisole, hydroquinone, pyrocatechol, t-butylcatechol, and phenothiazine; plasticizers; adhesion accelerators; fillers; anti-foaming agents; leveling agents; surface modifiers; antioxidants; ultraviolet absorbers; dispersing aids; anti-coagulants; catalysts; effect accelerators; cross-linking agents; and thickeners.

The amount of optional components other than the present polymerizable compound having an ethylenically unsaturated bond and the present oxime ester compound (excluding the above-mentioned other photopolymerization initiators, the alkali-developable compound optionally having an ethylenically unsaturated group, the inorganic compounds (fillers), the colorants, and the solvents) used in the photosensitive composition of the invention is not particularly limited and can be determined as appropriate depending on the usage thereof, but the total usage amount of such optional components is preferably equal to or below 50 parts by mass with respect to 100 parts by mass of the polymerizable compound having an ethylenically unsaturated bond.

The photosensitive composition of the invention may further contain other organic polymer(s) in addition to the polymerizable compound having an ethylenically unsaturated bond, to improve the characteristics of the cured products obtained. Examples of the organic polymer include polystyrene, polymethyl methacrylate, methyl methacrylate-ethyl acrylate copolymers, poly(meth)acrylic acid, styrene-(meth)acrylic acid copolymers, (meth)acrylic acid-methyl methacrylate copolymers, ethylene-vinyl chloride copolymers, ethylene-vinyl copolymers, polyvinyl chloride resins, ABS resins, nylon 6, nylon 66, nylon 12, urethane resins, polycarbonate, polyvinyl butyral, cellulose esters, polyacrylamide, saturated polyesters, phenol resins, phenoxy resins, polyamide-imide resins, polyamic acid resins, and epoxy resins. Preferred among the above are polystyrene, (meth)acrylic acid-methyl methacrylate copolymers, and epoxy resins.

The amount of the other organic polymer(s), if used, is preferably 10 to 500 parts by mass with respect to 100 parts by mass of the polymerizable compound having an ethylenically unsaturated bond.

The photosensitive composition of the invention may further contain, for example, a chain transfer agent, a sensitizer, a surfactant, a silane coupling agent, and/or a melamine compound.

Sulfur-containing compounds are generally used as the above-described chain transfer agent or sensitizer. Examples include: mercapto compounds, such as thioglycolic acid, thiomalic acid, thiosalicylic acid, 2-mercaptopropionic acid, 3-mercaptopropionic acid, 3-mercaptobutyric acid, N-(2-mercaptopropionyl)glycine, 2-mercaptonicotinic acid, 3-[N-(2-mercaptoethyl)carbamoyl]propionic acid, 3-[N-(2-mercaptoethyl)amino]propionic acid, N-(3-mercaptopropionyl)alanine, 2-mercaptoethanesulfonic acid, 3-mercaptopropanesulfonic acid, 4-mercaptobutanesulfonic acid, dodecyl (4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercaptobenzimidazole, 2-mercapto-3-pyridinol, 2-mercaptobenzothiazole, mercaptoacetic acid, trimethylolpropane tris(3-mercaptopropionate), and pentaerythritol tetrakis(3-mercaptopropionate); disulfide compounds obtained by oxidizing the above mercapto compounds; iodized alkyl compounds, such as iodoacetic acid, iodopropionic acid, 2-iodoethanol, 2-iodoethanesulfonic acid, and 3-iodopropanesulfonic acid; aliphatic polyfunctional thiol compounds, such as trimethylolpropane tris(3-mercaptoisobutyrate), butanediol bis(3-mercaptoisobutyrate), hexanedithiol, decanedithiol, 1,4-dimethylmercaptobenzene, butanediol bisthiopropionate, butanediol bisthioglycolate, ethylene glycol bisthioglycolate, trimethylolpropane tristhioglycolate, butanediol bisthiopropionate, trimethylolpropane tristhiopropionate, trimethylolpropane tristhioglycolate, pentaerythritol tetrakisthiopropionate, pentaerythritol tetrakisthioglycolate, trishydroxyethyl tristhiopropionate, diethylthioxanthone, diisopropylthioxanthone, the following compound No. C1, and trimercaptopropionate tris(2-hydroxyethyl)isocyanurate; and Karenz MT BD1, PE1, and NR1 available from Showa Denko K.K.

[Chem. 34]

Compound No. C1

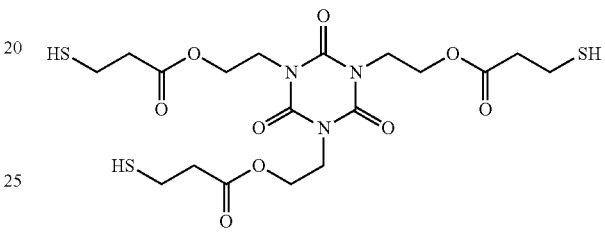

Examples of usable surfactants include: fluorine-containing surfactants, such as perfluoroalkylphosphoric esters and perfluoroalkylcarboxylic acid salts; anionic surfactants, such as higher fatty acid alkali salts, alkylsulfonic acid salts, and alkylsulfuric acid salts; cationic surfactants, such as higher amine halogen acid salts and quaternary ammonium salts; nonionic surfactants, such as polyethylene glycol alkyl ethers, polyethylene glycol fatty acid esters, sorbitan fatty acid esters, and fatty acid monoglycerides; amphoteric surfactants, and silicone surfactants. These surfactants may be used in combination.

Examples of usable silane coupling agents include those available from Shin-Etsu Chemical Co., Ltd., and among them, silane coupling agents having an isocyanate, methacryloyl, or epoxy group, such as KBE-9007, KBM-502, and KBE-403, can suitably be used.

Examples of the melamine compound include compounds wherein all or some (at least two) of the active methylol groups ($CH_2OH$ groups) in a nitrogen-containing compound, such as (poly)methylol melamine, (poly)methylol glycoluril, (poly)methylol benzoguanamine, or (poly)methylol urea, have been alkyletherified.

Examples of alkyl groups constituting the alkyl ether include methyl, ethyl, butyl, etc., which may all be the same or may be different from one another. Non-alkyletherified methylol groups may be self-condensed within a single molecule, or those of two molecules may undergo condensation to form an oligomer component.

Specifically, it is possible to use, for example, hexamethoxymethylmelamine, hexabutoxymethylmelamine, tetramethoxymethylglycoluril, or tetrabutoxymethylglycoluril.

Preferred among the above are alkyletherified melamines, such as hexamethoxymethylmelamine and hexabutoxymethylmelamine.

The photosensitive composition of the invention can be applied to a substrate, such as soda glass, quartz glass, semiconductor substrates, metals, paper, or plastics, using any known means for application, such as a spin coater, a roll coater, a bar coater, a die coater, a curtain coater, various printing techniques, and dipping. The photosensitive composition may temporarily be applied to a carrier substrate, such as a film, and then transferred to another substrate. The application method therefor is not limited.

Examples of energy rays usable for curing the photosensitive composition of the invention include high-energy rays such as electron beams, X rays, ionizing radiations, and electromagnetic-wave energy with wavelengths ranging from 2000 to 7000 angstroms obtained from light sources such as ultra-high-pressure-, high-pressure-, medium-pressure-, or low-pressure mercury lamps, mercury-vapor arc lamps, xenon arc lamps, carbon arc lamps, metal halide lamps, fluorescent lamps, tungsten lamps, excimer lamps, bactericidal lamps, light-emitting diodes, CRTs, etc. Preferable light sources include ultra-high-pressure mercury lamps, mercury-vapor arc lamps, carbon arc lamps, xenon arc lamps, etc., that emit light in the wavelength range from 300 to 450 nm.

Using laser beams as the light source for exposure is also advantageous, because direct laser imaging which directly forms images from digital information stored in e.g. computers, without using a mask, can improve productivity as well as resolution and positional accuracy. Laser beams within the wavelength range from 340 to 430 nm can suitably be used, but various lasers that emit light within the visible to infrared region, such as excimer lasers, nitrogen lasers, argon ion lasers, helium-cadmium lasers, helium-neon lasers, krypton ion lasers, various semiconductor lasers, and YAG lasers, may also be used. In case of using these types of lasers, sensitizing dyes are added to absorb light in the visible to infrared region.

The photosensitive composition of the invention has unlimited application. It finds use in, for example: photocuring paints or varnishes; photocuring adhesives; printed boards; color filters for liquid crystal color display devices, such as TV monitors, PC monitors, personal digital assistances, and digital cameras; color filters for CCD image sensors; electrode materials for plasma display panels; powder coatings; printing inks; printing plates; adhesives; compositions for dental use; gel coats; photoresists for electronics; electroplating resists; etching resists; dry films; soldering resists; resists for manufacturing color filters of various displays or for forming structures in the manufacture of plasma display panels, electroluminescent displays, and LCDs; encapsulating compositions for electric/electronic components; solder resists; magnetic recording materials; fine machine parts; waveguides; optical switches; plating masks; etching masks; color test systems; glass fiber cable coatings; screen printing stencils; materials for making a three-dimensional object by stereolithography; holographic recording materials; image recording materials; fine electronic circuits; decolorizing materials; decolorizing materials for image recording materials; decolorizing materials for image recording materials using microcapsules; photoresist materials for printed wiring boards; photoresist materials for direct imaging using UV and visible lasers; and photoresist materials or protective layers used to form dielectric layers in the fabrication of multilayered printed circuit boards.

The photosensitive composition of the invention can also be used for forming spacers for LCD panels and for forming protrusions for vertical-alignment LCD elements. The photosensitive composition is particularly useful for simultaneously forming spacers and protrusions for vertical-alignment LCD elements.

The spacers for LCD panels are preferably produced through (1) a step of forming, on a substrate, a film consisting of the photosensitive composition of the present invention, (2) a step of irradiating the film via a mask having a predetermined pattern thereon, (3) a post-exposure baking step, (4) a post-exposure film developing step, and (5) a post-development film heating step.

The photosensitive (colored) composition of the invention, if it contains an ink repellent agent, is also useful as a partition-wall-forming resin composition for use in inkjet processing. Such a composition is used for color filters, and preferably for partition walls for inkjet color filters particularly with profile angles of 50° or above. Fluorine-containing surfactants as well as compositions containing fluorine-containing surfactants can suitably be used as the ink repellent agent.

An optical element can be manufactured by forming, on a transfer recipient, partition walls using the photosensitive composition of the invention to partition the transfer recipient, and supplying liquid droplets into the recesses formed on the partitioned transfer recipient through inkjet processing, to form image regions thereon. It is preferable that the liquid droplets contain a coloring agent and that the image regions are thus colored. A preferably-used optical element is manufactured according to the above-described optical-element manufacturing method and thus has, on a substrate, at least a group of pixels consisting of a multitude of the colored regions, and partition walls partitioning the colored regions in the pixels group.

The photosensitive composition of the invention can also be used as compositions for protection films and insulation films, and may thus contain an ultraviolet absorber, alkylated and/or acrylated melamine, mono- or difunctional (meth) acrylate monomers containing alcoholic hydroxyl groups in their molecules, and/or silica sol.

A preferable example of a photosensitive resin composition for a protective film or an insulation film may contain, as main components:

(A) a carboxyl-group-containing resin that is obtained by reacting a diol compound with a polyhydric carboxylic acid and that has a weight-average molecular weight of 2,000 to 40,000 and an acid value of 50 to 200 mg-KOH/g;

(B) an unsaturated compound containing at least one photopolymerizable ethylenically unsaturated bond in each molecule;

(C) an epoxy compound; and (D) a photopolymerization initiator, wherein, the composition preferably contains 10 to 40 parts by weight of component (C) and 0.01 to 2.0 parts by weight of component (D) with respect to 100 parts by weight as a total of component (A) and component (B), and preferably contains the compound represented by general formula (I) as the photopolymerization initiator of component (D).

The insulation film is used as an insulating resin layer in a laminate having the insulating resin layer disposed on a peelable support. The laminate is preferably developable with an alkaline aqueous solution, and the insulating resin layer preferably has a thickness of 10 to 100 μm.

The photosensitive composition of the invention, if it contains inorganic materials (inorganic compounds), can also be used as a photosensitive paste composition. The photosensitive paste composition may be used for forming baked patterns of plasma display panels, such as partition wall patterns, dielectric patterns, electrode patterns, and black matrix patterns.

EXAMPLES

The present invention will now be described in further detail below according to Examples and Comparative Examples. The invention, however, is not to be limited thereto.

Example 1

Production of Compound No. 2

Step 1: Acylation

To a solution containing 92 g of dichioroethane and 21.7 g (163 mmol) of aluminum chloride was added 15 g (65 mmol) of 4-(phenylthio)benzoic acid, and then 9.0 g (97 mmol) of propionyl chloride was dropped thereto at a temperature of 6° C. or below. After stirring for 1 hour, the reaction solution was poured into ice water and then ethyl acetate was added thereto to separate it into the oil and aqueous phases, and the organic layer was washed with water. The organic layer was dried with anhydrous magnesium sulfate and then the solvent was removed, to yield 18.7 g of acylated compound a.

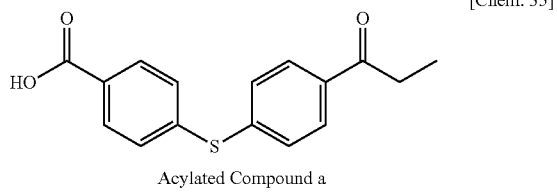

[Chem. 35]

Acylated Compound a

Step 2: Oximation

To a solution containing 10.0 g (35 mmol) of the acylated compound a obtained in Step 1 above, 3.6 g (35 mmol) of concentrated hydrochloric acid, and 30 g of dimethylformamide was added 5.4 g (52 mmol) of isobutyl nitrite, and the mixture was stirred for 3.5 hours at room temperature. After stirring, ethyl acetate and water were added to the reaction solution to separate it into the oil and aqueous phases, and the organic layer was washed with water. Hexane was added to the organic layer from which a solid matter had precipitated, and the solution was filtered. The filtered-out solid matter was dried under reduced pressure, to yield 8.6 g of oxime compound a.

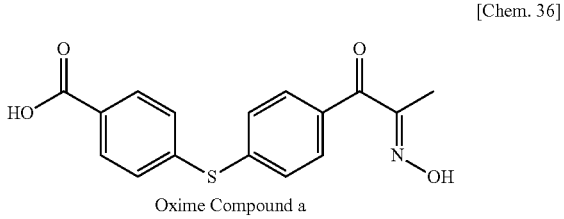

[Chem. 36]

Oxime Compound a

Step 3: Oxime Esterification

A solution containing 4.0 g (13 mmol) of the oxime compound a obtained in Step 2 above, 2.1 g (27 mmol) of pyridine, and 12 g of dimethylformamide was cooled to a temperature of −10° C. or below, and 1.6 g (15 mmol) of acetic anhydride was dropped thereto. Thereafter, the mixture was stirred for 2 hours at 5° C. After stirring, ethyl acetate and water were added to the reaction solution to separate it into the oil and aqueous phases, and the organic layer was washed with water. The organic layer was dried with anhydrous magnesium sulfate and then the solvent was removed, to yield 4.5 g of compound No. 2 of the present invention. Analyses results thereof are shown in Tables 1 to 3.

Examples 2 to 4

Production of Compounds Nos. 26 and 44 to 46

Compounds Nos. 26 and 44 to 46 of the present invention were produced from respectively-corresponding ketones according to the method described in Example 1. Analyses results thereof are shown in Tables 1 to 3.

TABLE 1

| | Oxime Ester Compound | λ max*[1] (nm) | Melting Point (° C.) | Decomposition Point (° C.) |
|---|---|---|---|---|
| Example 1 | Compound No. 2 | 291, 335 | 151 | 181 |
| Example 2 | Compound No. 26 | 335 | 96 | 202 |
| Example 3 | Compound No. 44 | 334 | 100 | 140 |
| Example 4 | Compound No. 45 | 292, 335 | 56 | 225 |
| Example 5 | Compound No. 46 | 336 | 130 | 143 |

*[1]The solvent used was CHCl$_3$.

TABLE 2

| | Oxime Ester Compound | IR Absorption Spectra (cm$^{-1}$) |
|---|---|---|
| Example 1 | Compound No. 2 | 2980, 2838, 2672, 2559, 1782, 1688, 1670, 1596, 1586, 1563, 1424, 1368, 1317, 1293, 1214, 1177, 1085, 994, 944, 905, 881, 757 |
| Example 2 | Compound No. 26 | 3529, 2937, 1782, 1652, 1596, 1581, 1491, 1364, 1300, 1329, 1253, 1217, 1173, 1191, 1083, 946, 908, 824, 746, 536 |
| Example 3 | Compound No. 44 | 3065, 1770, 1712, 1664, 1587, 1552, 1493, 1437, 1404, 1367, 1323, 1215, 1178, 1083, 996, 944, 884, 833, 749 |
| Example 4 | Compound No. 45 | 3508, 2947, 2872, 1780, 1717, 1668, 1586, 1400, 1367, 1276, 1203, 1179, 1109, 1084, 1014, 995, 944, 904, 887, 758 |
| Example 5 | Compound No. 46 | 3398, 1756, 1664, 1598, 1586, 1552, 1497, 1430, 1404, 1367, 1325, 1273, 1216, 1182, 1083, 997, 944, 884, 833, 749 |

TABLE 3

| | Oxime Ester Compound | Solvent for Measurement | $^1$H-NMR |
|---|---|---|---|
| Example 1 | Compound No. 2 | CDCl$_3$ | 2.22 (s, 3H), 2.23 (s, 3H), 7.44 (d, 2H), 7.53 (d, 2H), 7.96 (d, 2H), 7.98 (d, 2H) |
| Example 2 | Compound No. 26 | CDCl$_3$ | 2.25 (s, 3H), 2.26 (s, 3H), 4.00 (t, 2H), 4.13 (t, 2H), 6.98 (d, 2H), 7.08 (d, 2H), 7.48 (d, 2H), 7.94 (d, 2H) |
| Example 3 | Compound No. 44 | DMSO-d6 | 2.20 (s, 3H), 2.22 (s, 3H), 4.76 (s, 2H), 7.06 (d, 2H), 7.14 (d, 2H), 7.52 (d, 2H), 7.89 (d, 2H) |
| Example 4 | Compound No. 45 | CDCl$_3$ | 2.27 (s, 3H), 2.29 (s, 3H), 3.65 (t, 2H), 3.76 (t, 2H), 3.85 (t, 2H), 4.50 (t, 2H), |

TABLE 3-continued

| | Oxime Ester Compound | Solvent for Measurement | $^1$H-NMR |
|---|---|---|---|
| Example 5 | Compound No. 46 | CDCl$_3$ | 7.35 (d, 2H), 7.46 (d, 2H), 8.02 (d, 2H), 8.04 (d, 2H) 2.26 (s, 3H), 2.26 (s, 3H), 5.10 (s, 1H), 6.88 (d, 2H), 7.08 (d, 2H), 7.43 (d, 2H), 7.94 (d, 2H) |

Example 6

Production of Alkali-Developable Photosensitive Resin Composition No. 1

Step 1: Production of Alkali-Developable Resin

In a reaction vessel were placed 184 g of bisphenol fluorene epoxy resin (epoxy equivalent: 231), 58 g of acrylic acid, 0.26 g of 2,6-di-tert-butyl-p-cresol, 0.11 g of tetra-n-butylammonium bromide, and 23 g of propylene glycol-1-monomethyl ether-2-acetate, and the mixture was stirred for 16 hours at 120° C. The reaction solution was cooled to room temperature, and thereafter, 35 g of propylene glycol-1-monomethyl ether-2-acetate, 59 g of biphthalic anhydride, and 0.24 g of tetra-n-butylammonium bromide were added thereto and the mixture was stirred for 4 hours at 120° C. After stirring for 4 hours, 20 g of tetrahydrophthalic anhydride was added thereto, and the mixture was stirred for 4 hours at 120° C., for 3 hours at 100° C., for 4 hours at 80° C., for 6 hours at 60° C., and for 11 hours at 40° C. After stirring, 90 g of propylene glycol-1-monomethyl ether-2-acetate was added, to obtain alkali-developable resin No. 1 (Mw=5000; Mn=2100; acid value (of solids content): 92.7 mg-KOH/g) as a propylene glycol-1-monomethyl ether-2-acetate solution thereof.

Step 2: Preparation of Alkali-Developable Photosensitive Resin Composition No. 1

A mixture of 14.7 g of the alkali-developable resin No. 1 obtained in Step 1 of Example 6, 3.0 g of dipentaerythritol penta- and hexaacrylate ("Aronix M-402" available from Toagosei Co., Ltd.), 1.8 g of a 1% cyclohexanone solution of a surfactant "FZ-2122" (available from Nippon Unicar Co., Ltd.), 10.0 g of propylene glycol-1-monomethyl ether-2-acetate, and 20.2 g of cyclohexanone, was prepared. Then, 0.3 g of compound No. 2 obtained in Example 1 was added thereto, and the mixture was stirred thoroughly, to obtain alkali-developable photosensitive resin composition No. 1 of the present invention.

Example 7

Production of Alkali-Developable Photosensitive Resin Composition No. 2

Alkali-developable photosensitive resin composition No. 2 of the invention was prepared in the same way as in Step 2 of Example 6, except that compound No. 2 obtained in Example 1 was changed to compound No. 26 obtained in Example 2.

Comparative Example 1

Production of Alkali-Developable Photosensitive Resin Composition No. 3

Alkali-developable photosensitive resin composition No. 3, as a comparative product, was prepared in the same way as in Step 2 of Example 6, except that compound No. 2 obtained in Example 1 was changed to 2-benzyl-2-dimethylamino-1-(4-morpholinophenyl)-1-butanone.

Comparative Example 2

Production of Alkali-Developable Photosensitive Resin Composition No. 4

Alkali-developable photosensitive resin composition No. 4, as a comparative product, was prepared in the same way as in Step 2 of Example 6, except that compound No. 2 obtained in Example 1 was changed to ethanone,1-[9-ethyl-6-(2-methylbenzoyl)-9H-carbazol-3-yl]-,1-(O-acetyloxime).

Transmission Properties:

The transmission properties of the alkali-developable photosensitive resin compositions Nos. 1 to 4 were tested as follows.

Respective alkali-developable photosensitive resin compositions were coated on a glass substrate through spin-coating (for 2 seconds at 500 rpm; for 6 seconds at 800 rpm), and the coated substrate was pre-baked for 90 seconds at 90° C. using a hot plate. The pre-baked substrate was exposed to light of 150 mJ/cm$^2$ using a high-pressure mercury lamp as the light source, and was then subjected to post-baking for 30 minutes at 230° C. using an oven. The transmittance thereof at 380 nm was measured using an absorptiometer. The results are shown in Table 4.

TABLE 4

| Alkali-Developable Photosensitive Resin Composition | Transmittance (%) |
|---|---|
| No. 1 (Example 6) | 92 |
| No. 2 (Example 7) | 92 |
| No. 3 (Comparative Example 1) | 86 |
| No. 4 (Comparative Example 2) | 87 |

Table 4 reveals that the alkali-developable photosensitive resin compositions of Examples 6 and 7 which contain the oxime ester compounds of the present invention as photopolymerization initiators have higher transmittance than the alkali-developable photosensitive resin compositions of Comparative Examples 1 and 2 which contain, as photopolymerization initiators, compounds structured differently from the oxime ester compounds of the present invention.

Example 8

Production of Conductive Composition No. 1

A mixture of 14.1 g of the alkali-developable resin No. 1 obtained in Step 1 of Example 6, 7.1 g of dipentaerythritol penta- and hexaacrylate ("Aronix M-402" available from Toagosei Co., Ltd.), 0.05 g of a surfactant "BYK-323" (available from BYK Japan K.K.), 11.3 g of Texanol (2,2,4-trimethyl-1,3-pentanediol monoisobutyrate), 0.7 g of compound No. 2 obtained in Example 1, 3.1 g of glass frit, and 63.7 g of silver powder was prepared and was stirred together. After stirring, the mixture was kneaded using a triple roll mill, to obtain conductive composition No. 1, which is a photosensitive resin composition of the present invention.

Example 9

Production of Alkali-Developable, Colored Photosensitive Resin Composition No. 1

Step 1: Production of Blue Dispersion Liquid

To a 500-ml polyethylene container were placed 57.6 g of a blue pigment "Pigment blue 15:6", 20.0 g of a dispersing agent "Ajisper PB821" (available from Ajinomoto Fine-Techno Co., Inc.), 2.4 g of a dispersing aid "Solsperse 5000" (available from Avecia), and 320.0 g of propylene glycol-1-monomethyl ether-2-acetate, and the mixture was shaken for 10 hours with a paint conditioner using 350 g of zirconia beads having a particle size of 0.5 mm. Thereafter, the zirconia beads were filtered off, to obtain a blue dispersion liquid.

Step 2: Production of Alkali-Developable, Colored Photosensitive Resin Composition No. 1

A mixture of 10.63 g of the blue dispersion liquid obtained in Step 1 above, 2.98 g of the Alkali-developable resin No. 1 obtained in Step 1 of Example 6, 0.31 g of dipentaerythritol penta- and hexaacrylate ("Aronix M-402" available from Toagosei Co., Ltd.), 0.31 g of urethane acrylate "UN3320HS" (available from Negami Chemical Industrial Co., Ltd.), 0.30 g of a 1% cyclohexanone solution of a surfactant "BYK-323" (available from BYK Japan K.K.), 4.70 g of propylene glycol-1-monomethyl ether-2-acetate, and 10.36 g of cyclohexanone was prepared, and 0.41 g of the compound No. 2 obtained in Example 1 was added thereto and stirred, to obtain alkali-developable, colored photosensitive resin composition No. 1 of the present invention.

Example 10

Production of Alkali-Developable, Colored Photosensitive Resin Composition No. 2

Alkali-developable, colored photosensitive resin composition No. 2 of the invention was prepared in the same way as in Step 2 of Example 9, except that compound No. 2 obtained in Example 1 was changed to compound No. 26 obtained in Example 2.

Comparative Example 3

Production of Alkali-Developable, Colored Photosensitive Resin Composition No. 3

Alkali-developable, colored photosensitive resin composition No. 3, as a comparative product, was prepared in the same way as in Step 2 of Example 9, except that compound No. 2 obtained in Example 1 was changed to ethanone,1-[9-ethyl-6-(2-methylbenzoyl)-9H-carbazol-3-yl]-,1-(O-acetyloxime).

Comparative Example 4

Production of Alkali-Developable, Colored Photosensitive Resin Composition No. 4

Alkali-developable, colored photosensitive resin composition No. 4, as a comparative product, was prepared in the same way as in Step 2 of Example 9, except that compound No. 2 obtained in Example 1 was changed to 2-methyl-1-(4-methylthiophenyl)-2-morpholinopropan-1-one.

Comparative Example 5

Production of Alkali-Developable, Colored Photosensitive Resin Composition No. 5

Alkali-developable, colored photosensitive resin composition No. 5, as a comparative product, was prepared in the same way as in Step 2 of Example 9, except that compound No. 2 obtained in Example 1 was changed to 1,2-octanedione, 1-[4-(phenylthio)phenyl]-,2-(O-benzoyloxime).

Comparative Example 6

Production of Alkali-Developable, Colored Photosensitive Resin Composition No. 6

Alkali-developable, colored photosensitive resin composition No. 6, as a comparative product, was prepared in the same way as in Step 2 of Example 9, except that compound No. 2 obtained in Example 1 was changed to 2-benzyl-2-dimethylamino-1-(4-morpholinophenyl)-1-butanone.

Transmission Properties:

The transmission properties of the alkali-developable, colored photosensitive resin compositions Nos. 1 to 4 were tested as follows.

Respective alkali-developable, colored photosensitive resin compositions were coated on a glass substrate through spin-coating (for 7 seconds at 500 rpm), and the coated substrate was pre-baked for 90 seconds at 90° C. using a hot plate. The pre-baked substrate was exposed to light of 150 mJ/cm$^2$ using a high-pressure mercury lamp as the light source, and was then subjected to post-baking for 30 minutes at 230° C. using an oven. The transmittance thereof at 420 nm was measured using an absorptiometer. The results are shown in Table 5.

TABLE 5

| Alkali-Developable, Colored Photosensitive Resin Composition | Transmittance (%) |
|---|---|
| No. 1 (Example 9) | 62 |
| No. 2 (Example 10) | 62 |
| No. 3 (Comparative Example 3) | 58 |
| No. 4 (Comparative Example 4) | 28 |

Table 5 reveals that the alkali-developable, colored photosensitive resin compositions of Examples 9 and 10 which contain the oxime ester compounds of the present invention as photopolymerization initiators have higher transmittance than the alkali-developable, colored photosensitive resin compositions of Comparative Examples 3 and 4 which contain, as photopolymerization initiators, compounds structured differently from the oxime ester compounds of the present invention.

Outgassing Properties:

The outgassing properties of the alkali-developable, colored photosensitive resin compositions Nos. 1, 2, and 4 to 6 were tested as follows.

Respective alkali-developable, colored photosensitive resin compositions were coated on a glass substrate through spin-coating (for 7 seconds at 500 rpm), and the coated substrate was pre-baked for 90 seconds at 90° C. using a hot plate.

The pre-baked substrate was exposed to light of 100 mJ/cm$^2$ using a high-pressure mercury lamp as the light source. Approximately 3 mg of the thus-obtained film was scraped off, and the weight reduction rate thereof when held at 230° C. for 30 minutes was determined using a TG-DTA instrument (available from Seiko Instruments Inc.). The outgassing properties of each sample were evaluated from the weight reduction rate. The results are shown in Table 6.

TABLE 6

| Alkali-Developable, Colored Photosensitive Resin Composition | Weight Reduction Rate (%) |
| --- | --- |
| No. 1 (Example 9) | −7.7 |
| No. 2 (Example 10) | −7.3 |
| No. 4 (Comparative Example 4) | −15.6 |
| No. 5 (Comparative Example 5) | −11.9 |
| No. 6 (Comparative Example 6) | −11.9 |

Table 6 reveals that the oxime ester compounds of the present invention are superior in heat resistance and give off smaller amounts of sublimed products as compared to the compounds used in Comparative Examples 4 to 6.

Example 11

Production of Alkali-Developable, Colored Photosensitive Resin Composition No. 7

A mixture of 10.63 g of the blue dispersion liquid obtained in Step 1 of Example 9, 2.93 g of the alkali-developable resin No. 1 obtained in Step 1 of Example 6, 0.30 g of dipentaerythritol penta- and hexaacrylate ("Aronix M-402" available from Toagosei Co., Ltd.), 0.30 g of urethane acrylate "UN3320HS" (available from Negami Chemical Industrial Co., Ltd.), 0.05 g of a sensitizer "DETX-S" (available from Nippon Kayaku Co., Ltd.), 0.30 g of a 1% cyclohexanone solution of a surfactant "BYK-323" (available from BYK Japan K.K.), 4.72 g of propylene glycol-1-monomethyl ether-2-acetate, and 10.36 g of cyclohexanone was prepared, and 0.41 g of the compound No. 2 obtained in Example 1 was added thereto and stirred thoroughly, to obtain alkali-developable, colored photosensitive resin composition No. 7 of the present invention.

Example 12

Production of Alkali-Developable, Colored Photosensitive Resin Composition No. 8

Alkali-developable, colored photosensitive resin composition No. 8 of the invention was prepared in the same way as in Example 11, except that compound No. 2 obtained in Example 1 was changed to compound No. 26 obtained in Example 2.

Comparative Example 7

Production of Alkali-Developable, Colored Photosensitive Resin Composition No. 9

Alkali-developable, colored photosensitive resin composition No. 9, as a comparative product, was prepared in the same way as in Example 11, except that compound No. 2 obtained in Example 1 was changed to ethanone,1-[9-ethyl-6-(2-methylbenzoyl)-9H-carbazol-3-yl]-,1-(O-acetyloxime).

Comparative Example 8

Production of Alkali-Developable, Colored Photosensitive Resin Composition No. 10

Alkali-developable, colored photosensitive resin composition No. 10, as a comparative product, was prepared in the same way as in Example 11, except that compound No. 2 obtained in Example 1 was changed to 2-methyl-1-(4-methylthiophenyl)-2-morpholinopropan-1-one.

Comparative Example 9

Production of Alkali-Developable, Colored Photosensitive Resin Composition No. 11

Alkali-developable, colored photosensitive resin composition No. 11, as a comparative product, was prepared in the same way as in Example 11, except that compound No. 2 obtained in Example 1 was changed to 1,2-octanedione,1-[4-(phenylthio)phenyl]-,2-(O-benzoyloxime).

Comparative Example 10

Production of Alkali-Developable, Colored Photosensitive Resin Composition No. 12

Alkali-developable, colored photosensitive resin composition No. 12, as a comparative product, was prepared in the same way as in Example 11, except that compound No. 2 obtained in Example 1 was changed to 2-benzyl-2-dimethylamino-1-(4-morpholinophenyl)-1-butanone.

The photolithographic properties of the alkali-developable, colored photosensitive resin compositions Nos. 7 to 12 were evaluated as follows.

Respective alkali-developable, colored photosensitive resin compositions were coated on a glass substrate through spin-coating (for 7 seconds at 500 rpm), and the coated substrate was pre-baked for 90 seconds at 90° C. using a hot plate. The pre-baked substrate was exposed to a predetermined amount of light via a mask using a high-pressure mercury lamp as the light source. Using a 2.5% by mass sodium carbonate aqueous solution as a developer, the composition was developed for 45 seconds using a spin developer, was then washed thoroughly with water, and was subjected to post-baking for 30 minutes at 230° C. using an oven to fix the patterns. The following properties were evaluated. The test results are shown in Table 7.

Sensitivity:

The sensitivity of each alkali-developable, colored photosensitive resin composition was evaluated according to the following four-grade system.

Grade "a": The light-exposure amount at which the line width of the pattern formed exceeded the line width of the mask opening was 50 mJ/cm$^2$.

Grade "b": The above-defined light-exposure amount was 100 mJ/cm$^2$.

Grade "c": The above-defined light-exposure amount was 150 mJ/cm$^2$.

Grade "d": No pattern was formed even at 150 mJ/cm$^2$.

Adhesion Properties:

The adhesion properties of each alkali-developable, colored photosensitive resin composition were evaluated according to the following four-grade system.

Grade "A": The line width of the thinnest mask line in the pattern formed after exposure at 100 mJ/cm$^2$ and development was 3 μm or less.

Grade "B": The above-defined line width was 10 μm or less.

Grade "C": The above-defined line width was 15 μm or less.

Grade "D": The above-defined line width was 30 μm or above.

Residue:

The residue of each alkali-developable, colored photosensitive resin composition was evaluated according to the following two-grade system.

"None": No residue was observed at all on the glass surface after development.

"Present": Residues were observed over the entire surface.

TABLE 7

| Alkali-Developable, Colored Photosensitive Resin Composition | Sensitivity | Adhesion Properties | Residue |
|---|---|---|---|
| No. 7 (Example 11) | a | A | None |
| No. 8 (Example 12) | a | A | None |
| No. 9 (Comparative Example 7) | a | A | Present |
| No. 10 (Comparative Example 8) | d | D | None |
| No. 11 (Comparative Example 9) | b | B | None |
| No. 12 (Comparative Example 10) | d | D | None |

Table 7 shows that the oxime ester compounds of the present invention show no sign of residues and are thus superior in developability, as compared to the compound used in Comparative Example 7. Also, Table 7 reveals that the oxime ester compounds of the present invention are superior in sensitivity and adhesion properties, as compared to the compounds used in Comparative Examples 8 to 10.

The above results reveal that the oxime ester compounds of the present invention are superior in developability and in transmission properties in the visible region, as compared to the compounds used in Comparative Examples 2, 3, and 7.

Also, the oxime ester compounds of the invention are superior in transmission properties in the visible region, heat resistance, sensitivity, and adhesion properties, as compared to the compounds used in Comparative Examples 4 and 8.

Further, the oxime ester compounds of the invention are superior in heat resistance, sensitivity, and adhesion properties, as compared to the compounds used in Comparative Examples 5 and 9.

Furthermore, the oxime ester compounds of the invention are superior in transmission properties in the visible region, heat resistance, sensitivity, and adhesion properties, as compared to the compounds used in Comparative Examples 1, 6, and 10.

As shown above, the oxime ester compounds of the present invention have excellent transmission properties in the visible region, excellent heat resistance, and also excellent photolithographic properties, and are thus useful as photopolymerization initiators.

The invention claimed is:

1. An oxime ester compound represented by the following general formula (I):

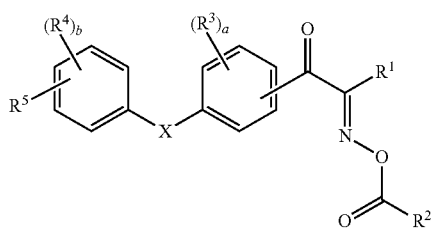

wherein, $R^1$ represents CN, a $C_{1-20}$ alkyl group, a $C_{6-30}$ aryl group, or a $C_{7-30}$ arylalkyl group;
a hydrogen atom in the substituents represented by $R^1$ may optionally be substituted by $OR^{21}$, $COR^{21}$, $SR^{21}$, a halogen atom, or $COOR^{21}$;
$R^{21}$ represents a hydrogen atom, or a $C_{1-20}$ alkyl group;
$R^2$ represents $R^{11}$;
$R^{11}$ represents a $C_{1-20}$ alkyl group, a $C_{6-30}$ aryl group, or a $C_{7-30}$ arylalkyl;
a hydrogen atom in the substituents represented by $R^{11}$ may optionally be substituted by a halogen atom;
an alkylene portion in the substituents represented by $R^1$, $R^{11}$, and $R^{21}$ may be interrupted 1 to 5 times by —O—, —S—, —COO—, —OCO—, or —$NR^{24}$—;
$R^{24}$ represents a hydrogen atom, a $C_{1-20}$ alkyl group, a $C_{6-30}$ aryl group, or a $C_{7-30}$ arylalkyl group;
an alkyl portion in the substituents represented by $R^{11}$ and $R^{21}$ may have a branched side chain or may be cyclopentyl or cyclohexyl;
$R^3$ and $R^4$ each independently represent $R^{11}$, $OR^{11}$, CN, hydroxyl group, or a halogen atom;
a and b each independently represent an integer of 0 to 4;
X represents a sulfur atom; and
$R^5$ represents OH, COOH, or a group represented by the following general formula (II);

wherein, $Z^1$ is a bonding hand and represents —O—, —S—, —OCO—, or —COO—;
$Z^2$ is a bonding hand and represents a $C_{1-20}$ alkyl group, a $C_{6-30}$ aryl group, or a $C_{7-30}$ arylalkyl group, each of which being substituted by one to three of $R^6$;
an alkylene portion in the bonding hand represented by $Z^2$ may be interrupted 1 to 5 times by —O—, —S—, —COO—, or —OCO—; an alkylene portion in the bonding hand represented by $Z^2$ may have a branched side chain or may be cyclohexylene;
$R^6$ represents $OR^{41}$ or $COOR^{41}$;
$R^{41}$ represents a hydrogen atom; and
c represents an integer of 1 to 3.

2. The oxime ester compound according to claim 1, wherein $Z^1$ in the general formula (II) is —O— or —OCO—.

3. The oxime ester compound according to claim 1, wherein $R^6$ in the general formula (II) is OH or COOH; and c in the formula is 1.

4. The oxime ester compound according to claim 1, wherein $Z^2$ in the general formula (II) is a $C_{1-20}$ alkyl group substituted by one to three of $R^6$; and the alkylene portion in the alkyl group may be interrupted 1 to 5 times by —O—, —OCO—, or —COO—.

5. The oxime ester compound according to claim 1, wherein $R^5$ in the general formula (I) is OH or COOH.

6. A photopolymerization initiator including the oxime ester compound according to claim 1.

7. A photosensitive composition, comprising the photopolymerization initiator according to claim 6 and a polymerizable compound having an ethylenically unsaturated bond.

8. The photosensitive composition according to claim 7, further containing an inorganic compound.

9. An alkali-developable photosensitive resin composition, comprising the photosensitive composition according to claim 7 and an alkali-developable compound that may optionally have an ethylenically unsaturated group.

10. The alkali-developable photosensitive resin composition according to claim 9, further containing an inorganic compound.

11. An alkali-developable, colored photosensitive resin composition, comprising the alkali-developable photosensitive resin composition according to claim 9 and a colorant.

12. A cured product produced by irradiating the photosensitive composition according to claim 7 with energy rays.

13. The oxime ester compound according to claim 2, wherein $R^6$ in the general formula (II) is OH or COOH; and c in the formula is 1.

14. The oxime ester compound according to claim 2, wherein $Z^2$ in the general formula (II) is a $C_{1-20}$ alkyl group substituted by one to three of $R^6$; and the alkylene portion in the alkyl group may be interrupted 1 to 5 times by —O—, —OCO—, or —COO—.

15. The oxime ester compound according to claim 3, wherein $Z^2$ in the general formula (II) is a $C_{1-20}$ alkyl group substituted by one to three of $R^6$; and the alkylene portion in the alkyl group may be interrupted 1 to 5 times by —O—, —OCO—, or —COO—.

16. A photopolymerization initiator including the oxime ester compound according to claim 2.

17. A photopolymerization initiator including the oxime ester compound according to claim 3.

18. A cured product produced by irradiating the alkali-developable photosensitive resin composition according to claim 9 with energy rays.

19. A cured product produced by irradiating the alkali-developable, colored photosensitive resin composition according to claim 11 with energy rays.

* * * * *